(12) United States Patent
Al-Sadah et al.

(10) Patent No.: US 11,574,792 B2
(45) Date of Patent: *Feb. 7, 2023

(54) BEAM GENERATION SYSTEM INCLUDING VACUUM PUMP AND LIQUID TARGET

(71) Applicant: King Fahd University of Petroleum and Minerals, Dhahran (SA)

(72) Inventors: Jihad Al-Sadah, Safwa (SA); Jafar Albinmousa, Al-Hasa (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/405,155

(22) Filed: Aug. 18, 2021

(65) Prior Publication Data
US 2021/0383999 A1 Dec. 9, 2021

Related U.S. Application Data

(63) Continuation of application No. 16/742,472, filed on Jan. 14, 2020, now Pat. No. 11,170,965.

(51) Int. Cl.
*H01J 35/12* (2006.01)
*H01J 35/18* (2006.01)
*G01N 23/04* (2018.01)

(52) U.S. Cl.
CPC .............. *H01J 35/13* (2019.05); *H01J 35/18* (2013.01); *G01N 23/04* (2013.01);
(Continued)

(58) Field of Classification Search
CPC ......... H01J 2235/082; H01J 2235/1204; H01J 2235/1279; H01J 35/13; H01J 35/18
See application file for complete search history.

(56) References Cited

U.S. PATENT DOCUMENTS 6,185,277 B1 * 2/2001 Harding .................. H01J 35/18
378/143
6,560,313 B1 5/2003 Harding et al.
(Continued)

OTHER PUBLICATIONS

Harding, et al.; Liquid metal anode X-ray tubes and their potential for high continuous power operation; Radiation Physics and Chemistry 67; pp. 7-14; Oct. 20, 2002; 8 Pages.

*Primary Examiner* — Chih-Cheng Kao
(74) *Attorney, Agent, or Firm* — Oblon, McClelland, Maier & Neustadt, L.L.P.

(57) ABSTRACT

A system for generating X-ray beams from a liquid target includes a vacuum chamber, a diamond window assembly, an electron source, a target material flow system, and an X-ray detector/imager. An electron beam from the electron source travels through the diamond window assembly and into a dynamic target material of the flow system. Preferably, the dynamic target material is lead bismuth eutectic in a liquid state. Upon colliding with the dynamic target material, X-rays are generated. The generated X-rays exit through an X-ray exit window to be captured by the X-ray detector/imager. Since the dynamic target material is constantly in fluid motion within a pipeline of the flow system, the electron beam always has a new target area which is at a controlled operational temperature and thus, prevents overheating issues. By providing a small focus area for the electron beams, the overall imaging resolution of the X-rays is also improved.

4 Claims, 31 Drawing Sheets

(52) U.S. Cl.
   CPC . *H01J 2235/082* (2013.01); *H01J 2235/1204* (2013.01); *H01J 2235/1279* (2013.01)

(56) References Cited

U.S. PATENT DOCUMENTS

| | | | |
|---|---|---|---|
| 6,647,094 B2 | 11/2003 | Harding et al. | |
| 6,711,233 B2 | 3/2004 | Hertz et al. | |
| 7,412,032 B2 | 8/2008 | Harding | |
| 11,170,965 B2 * | 11/2021 | Al-Sadah | H01J 35/13 |
| 2005/0213711 A1 * | 9/2005 | Ukita | H01J 35/12 |
| | | | 378/141 |
| 2011/0268237 A1 * | 11/2011 | Holden | G21G 1/10 |
| | | | 376/108 |
| 2012/0057680 A1 | 3/2012 | Hemberg et al. | |

* cited by examiner

BEAM GENERATION SYSTEM INCLUDING VACUUM PUMP AND LIQUID TARGET

CROSS-REFERENCE TO RELATED APPLICATIONS

The present application is a Continuation of U.S. application Ser. No. 16/742,472, pending, having a filing date of Jan. 14, 2020.

BACKGROUND

Field of the Invention

The present disclosure relates to a method and system for X-ray beam generation from a liquid target. The method and system of the present disclosure provides improved X-ray imaging resolution and heat reduction.

Description of the Related Art

The use of X-rays has a significant impact on the healthcare industry. Identifying bone fractures, imaging soft tissues, and cancer radiation diagnostics are some instances where X-rays are used in the healthcare industry. Diagnostic X-rays are generally within a range of 20 kiloelectron volt (keV)-150 keV whereas X-rays used for radiation therapy are usually in the range of 4-20×1000 keV. Additionally, X-rays are also used in other industries such as the oil industry where X-rays are used to image rock samples. X-rays can also be used to image material defects. In doing so, a higher resolution, which is greater than the resolution used in medical imaging, is required. In instances where higher resolution is required, the physical constraints related to X-ray generation may lead to a reduction in overall production power. High resolution imaging at a higher power will lead to a reduction in imaging time as well. Thus, a system that generates high resolution images at a high production power value is required to address the drawbacks associated with conventional X-ray generation methods. In general, if the resolution is high, the focal spot is considerably small and the power must be lowered.

More specifically, power is defined as a ratio between energy and time (power=energy/time), and intensity is defined as a ratio between power and area (intensity=power/area). A target material can only handle a limited intensity. Therefore, if the resolution is high and the resulting focal spot area is small, the intensity can be maintained at accepted values by lowering the power.

In order to generate X-rays, electrons are initially accelerated in a vacuum by an electric field towards a metal target. When the electrons decelerate within the metal, X-rays are emitted. Electron deceleration can occur in two routes.

In a first route, named Bremsstrahlung radiation, electromagnetic radiation is produced by the deceleration of a charged particle when deflected by another charged particle, typically an electron by an atomic nucleus. The moving particle loses kinetic energy, which is converted into radiation (i.e., a photon), thus satisfying the law of conservation of energy. The term is also used to refer to the process of producing the radiation. Bremsstrahlung has a continuous spectrum, which becomes more intense and whose peak intensity shifts toward higher frequencies as the change of the energy of the decelerated particles increases. Since the distance between the nucleus and the electrons cannot be controlled, the X-ray energy is random yet statistically predictable.

In a second route, named characteristic radiation, X-rays are produced when an element is bombarded with high-energy particles, which can be photons, electrons or ions (such as protons). When the incident particle strikes a bound electron (the target electron) in an atom, the target electron is ejected from the inner shell of the atom. After the electron has been ejected, the atom is left with a vacant energy level, also known as a core hole. Outer-shell electrons then fall into the inner shell, emitting quantized photons with an energy level equivalent to the energy difference between the higher and lower states. Each element has a unique set of energy levels, and thus the transition from higher to lower energy levels produces X-rays with frequencies that are characteristic to each element.

Generally, when X-ray beams are to be generated, an electron beam is accelerated and then plunged into a metal target such that both X-ray emitting methods can operate. If the desired energy range for the X-ray is within the range of 10 kiloelectron volt (keV)-150 keV, a majority of the energy from the electrons is converted to heat, and less than 1% is converted into X-ray radiation. A target energy range of 20 keV-150 keV is preferred for better imaging contrast of human tissue based on thickness and atomic composition (electron density). The X-ray energy required to generate adequate contrast at reasonable penetration depends on the imaging subject. In particular, the thinner the imaging subject, the lesser X-ray energy is required. For example, when imaging a human female breast during mammography, wherein the thickness of the breast is approximately 4 centimeters (cm)-5 cm, the imaging process is performed with an energy level within the range of 20 keV-40 keV.

The X-ray exposure, R, is approximately given by the formula $$R = \text{constant} * T_o^2 * Z * N_e,$$

Where,
$N_e$—Number of incoming electrons;
$T_o$—Energy of the incoming electrons;
Z—Atomic number of the target bombarded by the incoming electrons; See Frank Attix, "Introduction to Radiological Physics and Radiation Dosimetry", Wiley-VCH 1991, incorporated herein by reference in its entirety.

When generating X-ray beams in the medical field, the technological process involves generating an electron beam from a small hot filament positioned within a vacuum tube. The electron beam is accelerated to a desired kilovoltage (kV) level which is preferably within a range of 20 kV-160 kV. The electron beam is then focused onto a small rectangular shape on a solid target, wherein the solid target is generally tungsten. The dimensions of the rectangular shape can be, but are not limited to, 1.2 millimeters (mm), 0.6 mm, 0.3 mm, and 0.1 mm. The dimensions can vary according to the line of focus principle, which determines the angle in which the target is positioned at relative to the incident electron beam.

For imaging purposes, to generate an X-ray image, the X-ray beams need to be generated from a point source. The point source is obtained by focusing the electron beams into a small focus region such that the small focus region turns into the X-ray source after the interaction with the electron beams. The imaging resolution gets better as the focus region gets smaller. However, cooling the focus region becomes a challenge due to the concentrated thermal energy. Therefore, in fixed target systems as shown in FIG. 1A, the focus region has to be kept large to prevent heat related damage. The thermal capacity of the target that contains the focus region, the conductivity properties of the target, and the boiling point of the target are some of the factors that need to be considered when using a fixed target for X-ray generation.

As illustrated in FIG. 1B, rotating the target is one approach used to address heat related issues. By rotating the target, the electron beam contacts a region of the target that has been cooled down during rotation. Even though rotating the target has allowed smaller focus regions, implementing and maintaining mechanical systems that allow the target to rotate can be challenging. Moreover, having to limit the heat that is generated to be within the anode limits the overall length of the imaging session as well; see for example U.S. Pat. Nos. 7,852,987 and 8,259,905, each incorporated herein by reference in their entireties.

In view of the difficulties and drawbacks of existing X-ray generating methods, the present disclosure describes a system to generate X-rays that may result in comparatively better imaging resolution. To do so, the present disclosure describes a system that may be used to increase electron beam intensity by replacing the conventionally fixed electron beam target with a fluid target. The electron beam reaches the fluid target by passing through a diamond window with high thermal conductivity. The diamond window, which is solid and has high thermal conductivity, is in constant contact with the fluid target such that the fluid target maintains a temperature of the diamond window.

SUMMARY OF THE INVENTION

The system of the present disclosure includes a vacuum chamber, a thin diamond window assembly, an electron source, a target material flow system, and an X-ray detector/imager. The electron source and the thin diamond window assembly are positioned within the vacuum chamber. The thin diamond window assembly is integrated into the target material flow system which carries a dynamic target material used for X-ray beam generation. A high atomic number material such as lead bismuth eutectic may be selected as the dynamic target material. Since the dynamic target material is constantly flowing within a pipeline of the target material flow system, overheating issues related to conventional X-ray generation systems may be addressed. Moreover, since the electron beam is focused on a smaller target area the overall imaging quality resulting from the X-ray beams may be improved.

Keeping in mind that electron beams can be directed using electric or magnetic fields but x-ray beams cannot be directed in any easy way (e.g., there are no "x-ray optics" like lenses or reflectors), the electron source is aligned with the thin diamond window assembly such that the electron beam is directed to the thin diamond window assembly. Since the thin diamond window assembly is integrated into the target material flow system, the electron beam travels through a diamond sheet of the thin diamond window assembly and collides with the dynamic target material. A direction of the X-ray beam produced upon collision is towards an exit window of the vacuum chamber. To do so, the thin diamond window assembly is angularly positioned relative to the electron source. The X-ray detector/imager, which is positioned outside the vacuum chamber and also aligned with the exit window, is used to detect the X-ray beams.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

All illustrations of the drawings are for the purpose of describing selected embodiments of the present disclosure and are not intended to limit the scope of the present disclosure or accompanying claims.

The present disclosure describes a method and system that is used to generate X-ray beams from a liquid target material. Since the electron beam target is constantly flowing within a designated flow system, the overheating issues related to conventional X-ray beam generating systems are minimized and thus, the lifetime of the X-ray beam generating system may be extended. Furthermore, the regulated temperature of the liquid target material allows the electron beams to focus onto a smaller target area resulting in high resolution X-ray images. By using a high atomic number material such as a lead bismuth eutectic as the liquid target material, an increase in X-ray beam generation of approximately 12% may be achieved compared to the X-ray beam generation from a tungsten target. The use of the liquid target material may also aid in generating X-ray beams with a higher intensity that leads to less imaging time. When used for biological imaging, less imaging time is beneficial with motion artifacts that are generally known to degrade the resolution of an X-ray image by causing signal changes. X-ray beams with higher intensity can also reduce the overall imaging time in material science imaging and industrial imaging processes where X-rays are used as a non-destructive testing method to verify the internal structure and integrity of a specimen.

Figure 1A:
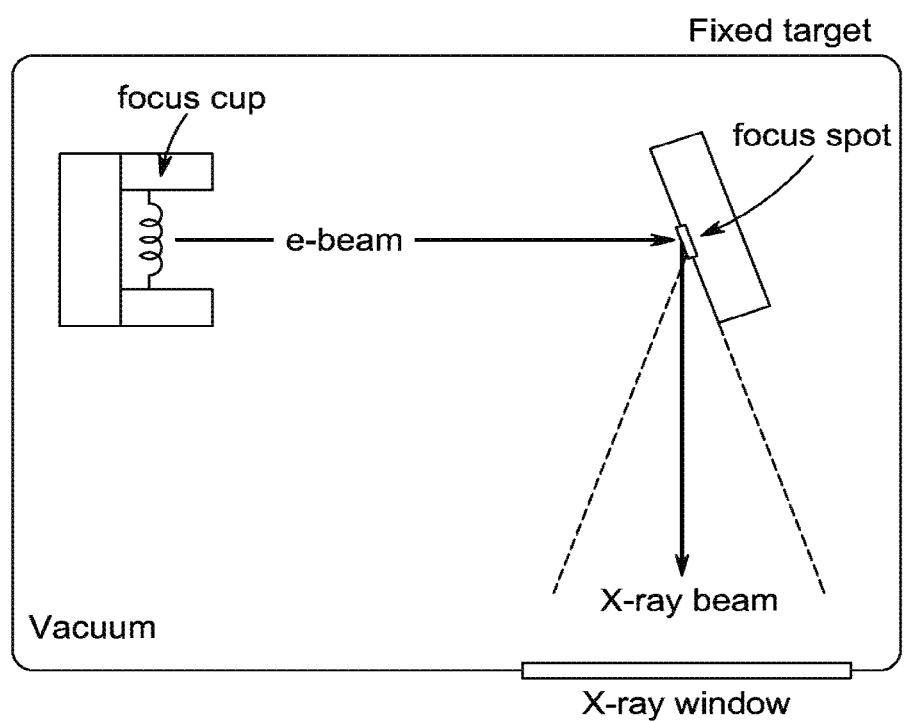
FIG. 1A is an illustration of X-ray beam generation from a fixed target.
Figure 1B:
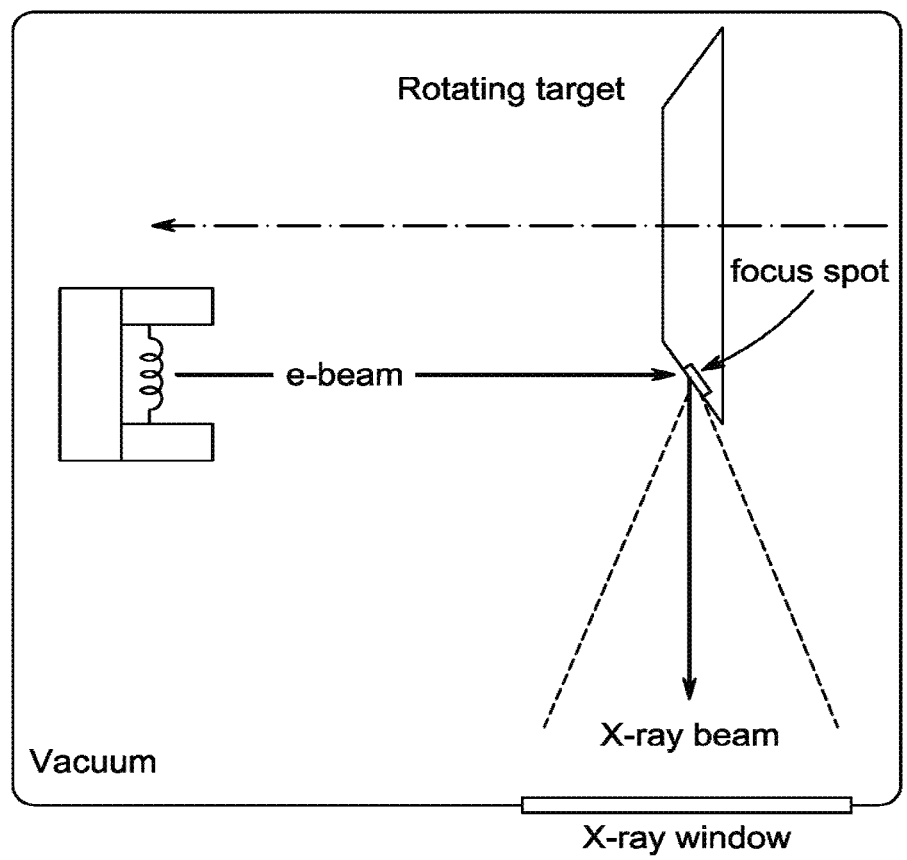
FIG. 1B is an illustration of X-ray beam generation from a rotating target.
Figure 2A:
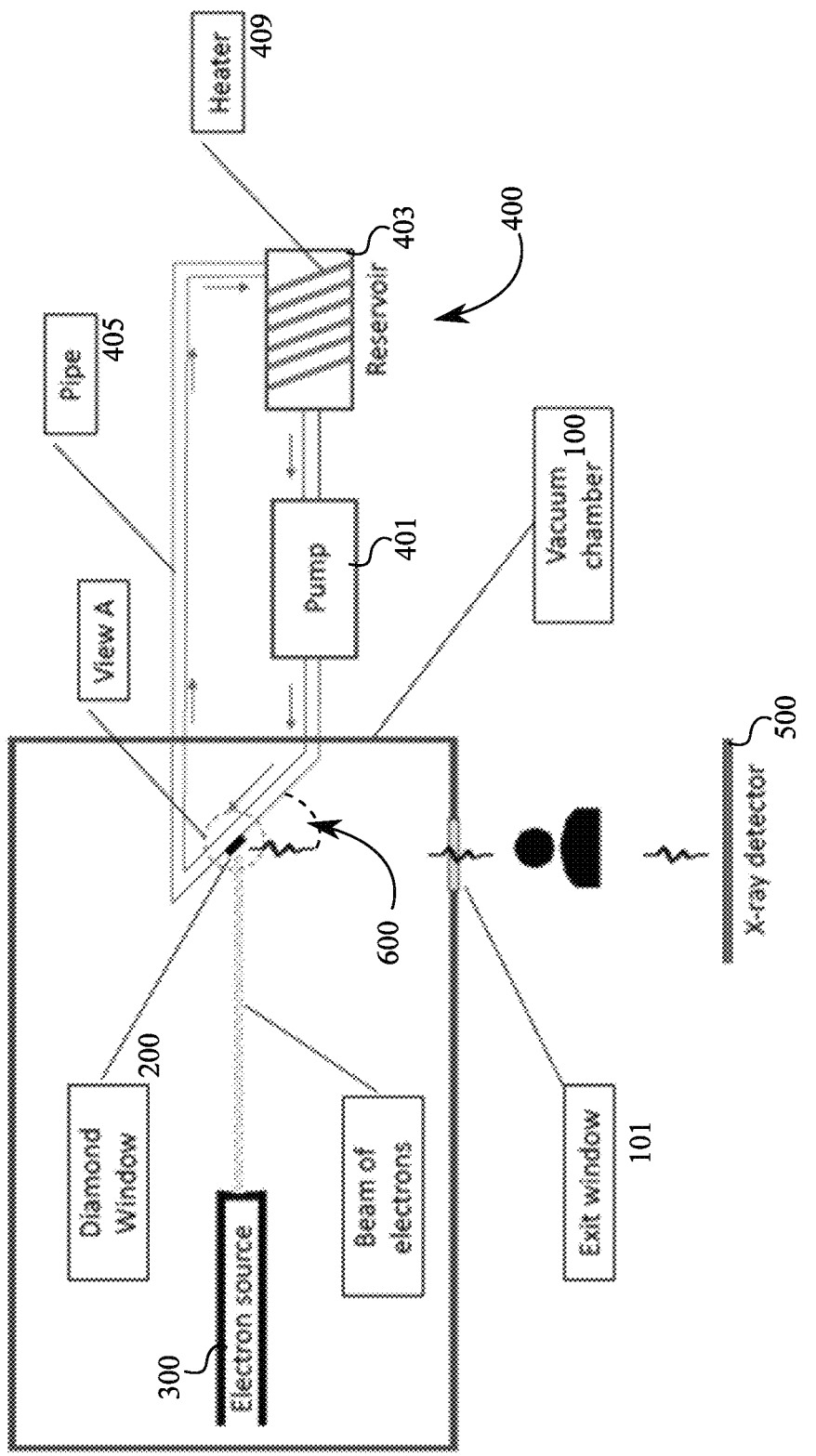
FIG. 2A is a schematic diagram of the system of the present disclosure.
Figure 2B:
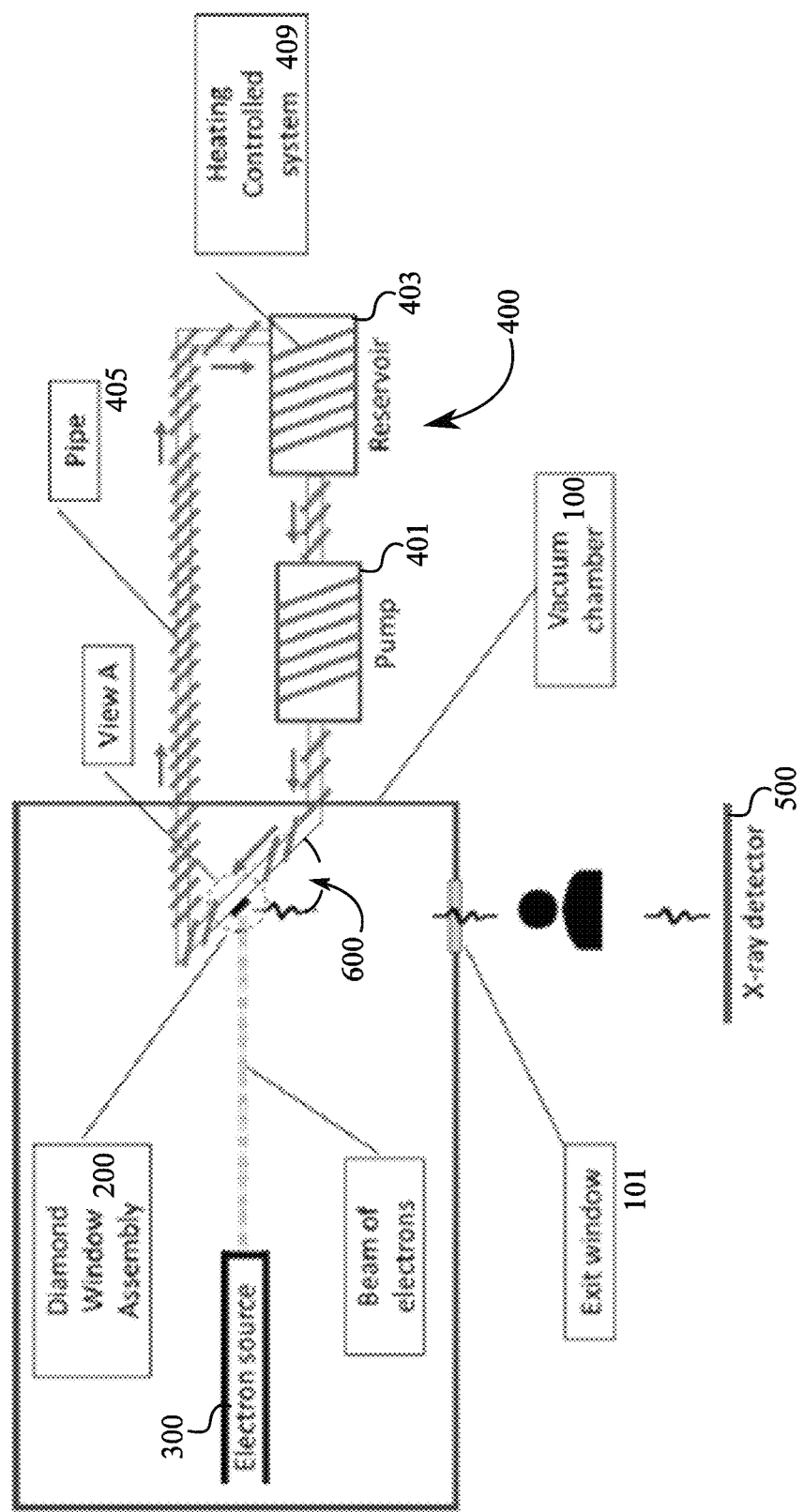
FIG. 2B is a schematic diagram of the system of the present disclosure, wherein a pipeline is covered by a heating coil of the temperature control unit.
Figure 3:
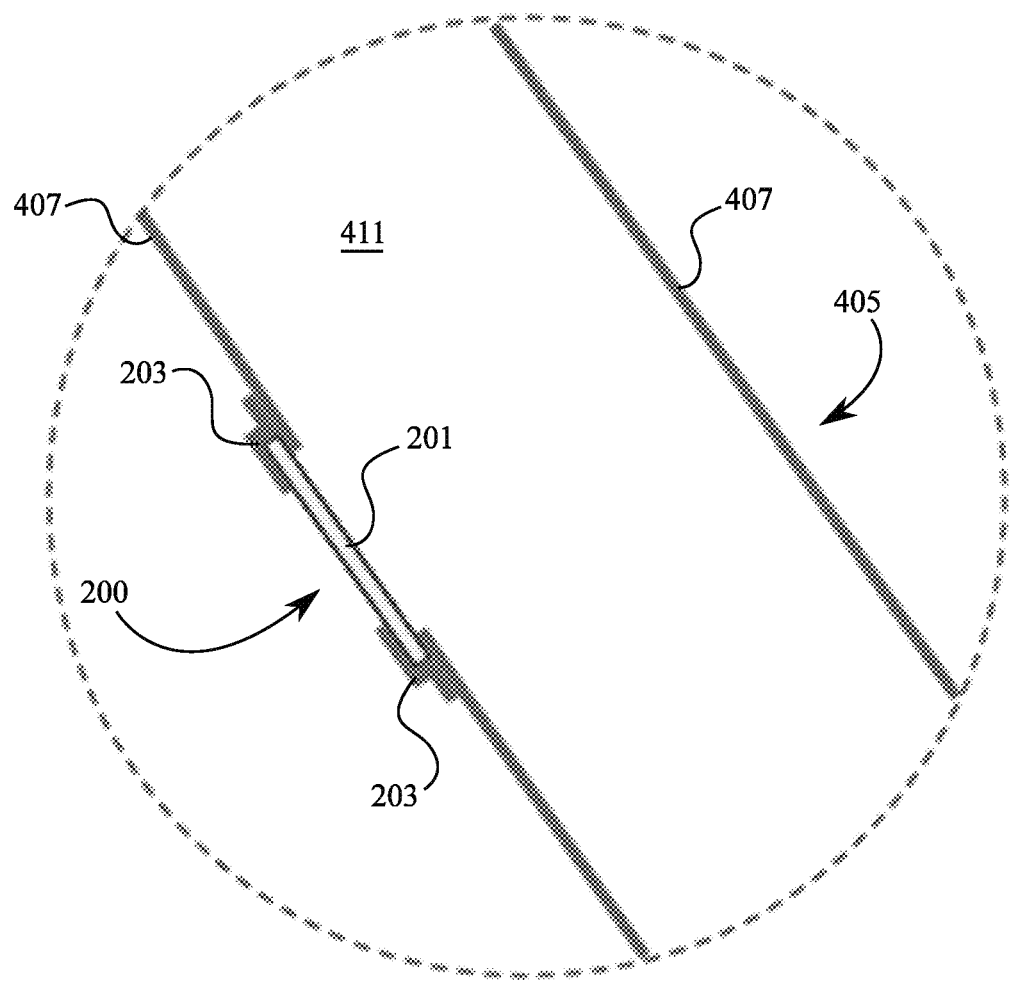
FIG. 3 is a detailed view of the thin diamond window assembly of the present disclosure.

As seen in FIG. 2A, FIG. 2B, and FIG. 3, the system of the present disclosure comprises a vacuum chamber 100, a thin diamond window assembly 200, an electron source 300, a target material flow system 400, and an X-ray detector/imager 500. The vacuum chamber 100 provides a non-oxidative environment for the cathode material to project electrons as an electron beam towards the anode. In addition, the vacuum prevents scattering of the electron beam by gas molecule which occurs if the vacuum is not in place. In order to do so, the electron source 300, which emits electrons as an electron beam, and the thin diamond window assembly 200, which allows the electron beam to collide with a dynamic target material 411, are positioned within the vacuum chamber 100. In this instance, the electron source 300 functions as the cathode whereas the dynamic target material 411 functions as the anode. The electron source 300 is positioned within the vacuum chamber 100 such that the electron beam is aligned with the thin diamond window assembly 200.

As described earlier, the vacuum prevents scattering of the electron beam. However, when the electron beam passes through the thin diamond window assembly 200, scattering may occur. A thinness of a diamond sheet 201 of the thin diamond window assembly 200 minimizes the scattering. Moreover, diamond having a low atomic number also minimizes scattering. Furthermore, the electron beam can be focused to counteract scattering while maintaining a direct line of sight between the cathode and the anode. In particular, the electron beam needs to strike the dynamic target material 411 at an angle such that the generated X-rays proceed towards an imaging subject through an X-ray exit window 101. For example, a normal incidence of the electron beam prevents the X-rays generated upon collision from exiting through the X-ray exit window due to self-attenuation at the anode.

If the electron beam is normal to the dynamic target material 411, a majority of the generated X-rays will be absorbed by the dynamic target material 411 with the exception of mega voltage beams where most of the radiation is in the forward direction and the target anode is considerably thin. Therefore, as seen in FIG. 2A and FIG.

Figure 2C:
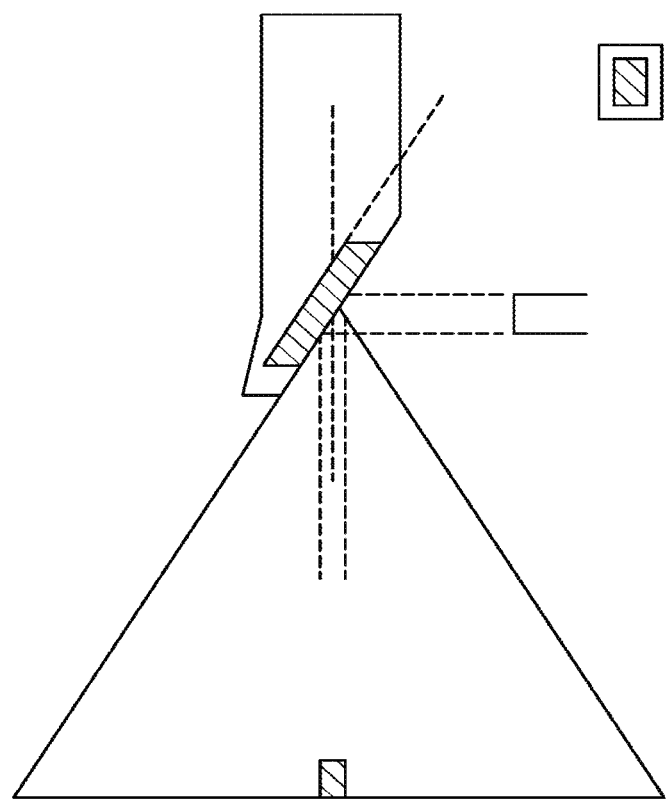
FIG. 2C is an illustration of the anode being angularly positioned at a large anode angle to the electron beam with a short filament length.
Figure 2D:
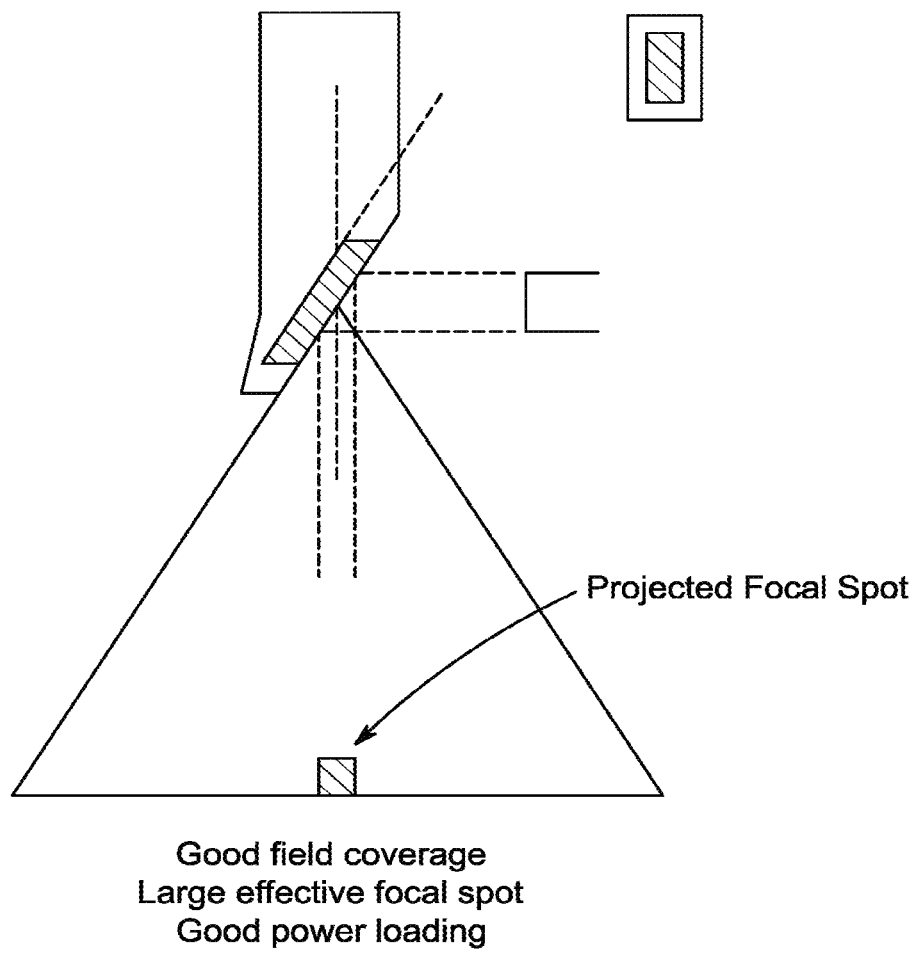
FIG. 2D is an illustration of the anode being angularly positioned at a large anode angle to the electron beam with a long filament length.
Figure 2E:
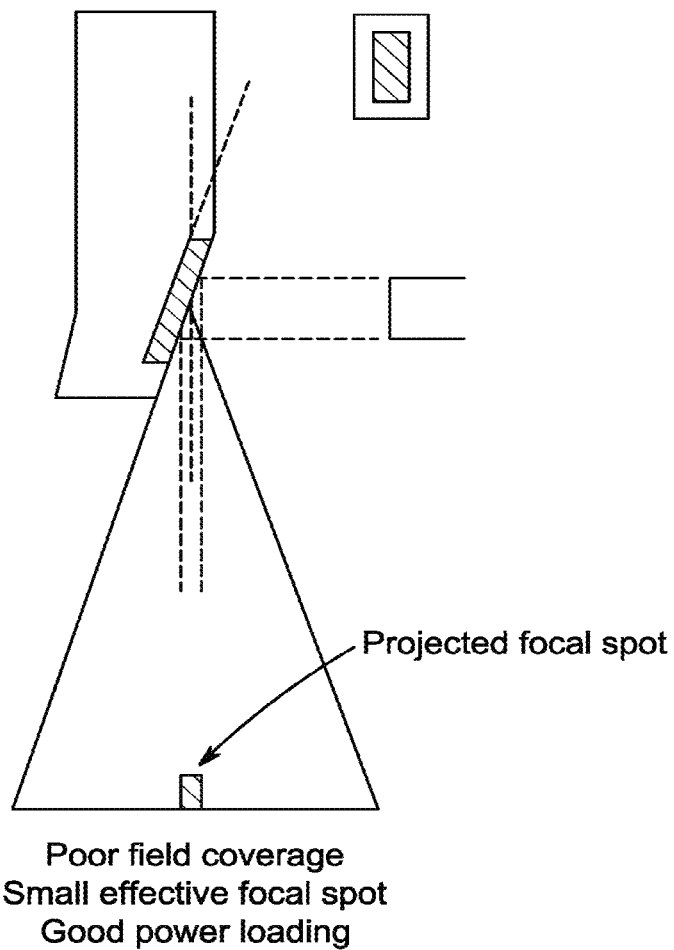
FIG. 2E is an illustration of the anode being angularly positioned at a small anode angle to the electron beam with a small filament length.

2B, the thin diamond window assembly 200 is angularly positioned at an anode angle 600 such that a tangent line along the dynamic target material 411 defines one edge of the generated X-ray field. FIGS. 2C-2E illustrate the field coverage variation of the X-ray beam according to the anode angle 600. The imaging subject is always positioned at a 90-degree angle to the electron beam as the electron beam is incident to the thin diamond window assembly 200 since most of the x-ray radiation is generated around the 90-degree angle. As seen in FIGS. 2C-2E, a tradeoff exists between the field coverage on the imaging side and the anode angle 600. The larger the angle the wider the field size is, and the better the power loading. However, the resolution diminishes due to the geometric projection of the focal spot.

As illustrated in FIG. 2C, when a large anode angle and a short filament length are used, satisfactory X-ray field coverage is achieved. However, a small effective focal spot resulting from the large anode angle and the small filament length limits the overall power loading. When a large anode angle and a long filament length are used as illustrated in FIG. 2D, satisfactory field coverage is achieved. However, a larger effective focal spot is required for higher power loading. When a small anode angle and a long filament length are used as illustrated in FIG. 2E, the overall field coverage is limited. However, the small effective focal spot resulting from the small anode angle and the long filament length allows high power loading. The anode angle 600 can be, but is not limited to, a value between a range of 5 degrees (°)-25°, preferably 10°-20°, or about 15°.

For the electron beam to pass through the thin diamond window assembly 200 and collide with the dynamic target material 411, which is in liquid state, the thin diamond window assembly 200 is integrated into the target material flow system 400 that maintains the flow of the dynamic target material 411.

A high atomic number material is used as the dynamic target material 411, wherein the high atomic number material results in a stronger radiative interaction with the electron beam such that a high yield of high energy X-rays are generated. In a preferred embodiment, a lead bismuth eutectic (LBE) is used as the dynamic target material 411. However, in other embodiments, alloys with relatively low melting temperatures of materials including, but not limited to, gallium, mercury, indium, tin, cadmium, lead, or bismuth, preferably excluding alkaline metals may be used as the dynamic target material 411.

When considering the properties of lead bismuth eutectic, lead (Pb) has an atomic number of 82, whereas bismuth (Bi) has an atomic number of 83. When considering the composition, lead bismuth eutectic has 44.5% of lead and 55.5% of bismuth. The density of lead bismuth eutectic can be expressed as 1106-1.293·T kilogram/cubic meter (kg/m$^3$), wherein T is the temperature in kelvins. The specific heat capacity, $C_p$, is 164.8−0.0394T+0.0000125T$^2$−45600T$^{-2}$ Joules per kilogram kelvin (J/kg-K), wherein the specific heat capacity may depend on the lead composition, when liquid lead bismuth eutectic has a lead composition between 40% and 60%. The thermal conductivity, K, is 3.284+ 0.001617T−2.305E-6T$^2$ Watts per meter kelvin (W/m-K). The viscosity, μ, is 0.000494exp (754.1/T) kilogram per meter per second (kg/m-s).

The dynamic target material 411, which is in a liquid state, preferably fulfills specific requirements to be used as a target material for the electron beam. For example, thermal conductivity, specific heat, and kinematic viscosity allow exceptionally good heat transport from the focal spot (the interaction zone of the electron-beam with the dynamic target material 411) to the outside of a pipeline 405 facilitating the flow of the dynamic target material 411. As described earlier, in order to get a high yield of high energy x-rays, it has to contain elements with high atomic numbers. The vapor pressure must be low enough to allow high temperatures sufficient to contain the liquid metal within the piping network. Additionally, other factors such as having a low melting point, which is preferably below room temperature, need to be considered when selecting the dynamic target material 411. Liquid lead bismuth eutectic has a melting point within a range of 397.7K-398.1K. Near the melting point, the density of a liquid metal generally shows an almost linear dependence on temperature. Pure lead has a melting point within a range 598K-601K, whereas pure bismuth has a melting point within a range of 543K-547K.

X-ray beams are generated from the radiative interactions of the electrons with the dynamic target material 411. After an X-ray beam is generated, to direct the X-ray beam towards the X-ray detector/imager 500, the thin diamond window assembly 200 and the target material flow system 400 are angularly positioned to the electron source 300. As a result, the X-ray beam generated from the deceleration of electrons is directed towards an X-ray exit window 101 of the vacuum chamber 100. In particular, the generated X-ray is directed along a path that is perpendicular to a projection path of the electron beam. The X-ray beam that passes through the X-ray exit window 101 towards the X-ray detector/imager 500 that is positioned externally and adjacent to the vacuum chamber 100. Moreover, the X-ray beam passes through an imaging subject when travelling towards the X-ray detector/imager 500. For detection purposes, the X-ray detector/imager 500 is linearly aligned with the X-ray exit window 101.

One of the primary purposes of having a small focal spot is to improve imaging resolution. When the generated X-rays reach the X-ray detector/imager 500, the X-ray detector/imager 500 develops the image. The X-ray detector/imager 500 can include, but is not limited to, films, image intensifiers, computed radiography techniques, and solid state array detectors. The solid state array detectors can be direct, where X-rays generate the charge that is read by a detector element, or indirect, where X-rays generate light that is detected by a light detector either directly or after optical processing.

The electron beam travels from the cathode to the anode within a vacuum. In a preferred embodiment, the vacuum chamber 100 providing the vacuum environment is a tube that has gases removed and sealed during manufacturing process. However, the type of vacuum chamber 100 may vary from one embodiment to another. For the transmission of electrons, ultra-high vacuum (UHV) conditions need to be satisfied. Therefore, the vacuum chamber 100 will require pressure values lower than about 10$^{-7}$ pascal or 100 nanopascals (10$^{-9}$ millibar, ~10$^{-9}$ torr), which can be achieved by pumping gas out of the vacuum chamber 100. Since one pump may not be able to operate from an atmospheric pressure value to a UHV pressure value, a series of different pumps is preferably used according to the appropriate pressure range of the pump. As a first step, a roughing pump, which is initially used to evacuate a vacuum system, clears a majority of the internal gas from the vacuum chamber 100. Next, one or more pumps that operate at low pressures are used to remove the remainder of the gas from the vacuum chamber 100. The low pressure pumps can be, but is not limited to, turbomolecular pumps, ion pumps, titanium sublimation pumps, non-evaporable getter (NEG) pumps, and cryopumps.

A turbomolecular pump works on the principle that gas molecules can be given momentum in a desired direction by repeated collision with a moving solid surface. In a turbomolecular pump, a rapidly spinning fan rotor 'hits' gas molecules from the inlet of the pump towards the exhaust in order to create or maintain a vacuum.

Ion pumps are capable of reaching pressures as low as $10^{-11}$ mbar. An ion pump first ionizes gas within the vessel it is attached to and employs a strong electrical potential, typically 3-7 kilo Volts (kV), which accelerates the ions to into the a solid electrode. Small bits of the electrode are sputtered into the chamber. Gasses are trapped by a combination of chemical reactions with the surface of the highly-reactive sputtered material, and being physically trapped underneath that material.

NEG pumps, based on the principle of metallic surface sorption of gas molecules, are mostly porous alloys or powder mixtures of Al, Zr, Ti, V and Fe. These pumps help establish and maintain vacuums by soaking up or bonding to gas molecules that remain within a partial vacuum through the use of materials that readily form stable compounds with active gases. Sintered onto the inner surface of high vacuum vessels, the NEG coating can be applied even to spaces that are narrow and hard to pump out, which makes NEG pumps very popular in particle accelerators where spacing is an issue.

A cryopump is a vacuum pump that traps gases and vapors by condensing them on a cold surface, but are only effective on some gases. The effectiveness depends on the freezing and boiling points of the gas relative to the temperature of the cryopump. Cryopumps are sometimes used to block particular contaminants, for example in front of a diffusion pump to trap backstreaming oil, or in front of a McLeod gauge to keep out water.

When considering the overall structure, the vacuum chamber 100 is preferably a glass or metal envelope that can maintain a vacuum environment for the cathode and the anode. Because the production of x-rays involves the interaction between filament electrons and the anode target, if any air were present, the electrons from the air would contribute to the electron stream, causing arcing and damage to the tube. The glass envelope variety is generally made of borosilicate glass because it is very heat resistant. However, as these tubes age, vaporized tungsten from the filament deposits on the inside of the glass (called "sun tanning" because of the bronze discoloration of the glass), which causes problems with arcing and damage. The metal envelope variety provides a constant electric potential between the electron stream from the cathode and the enclosure, thereby avoiding the arcing problem and extending tube life. The X-ray exit window 101 is designed to minimally interfere with the X-ray beam generated when the electrons collide with the dynamic target material 411. To do so, the X-ray exit window 101 is preferably made to have a small thickness, wherein the thickness can be, but is not limited to being within a range of 0.020 mm-0.050 mm, 0.025 mm-0.040 mm, and 0.025 mm-0.035 mm. The X-ray exit window 101 is preferably made from low atomic number materials to minimize x-ray scattering and/or absorption. The X-ray exit window 101 is also designed to withstand the pressure differential between the interior of the vacuum chamber 100 and the atmospheric pressure outside the vacuum chamber 100. A wall thickness of the vacuum chamber 100 can be, but is not limited to, being within a range between 2 mm-5 mm.

Preferably, the vacuum chamber 100 is positioned within a protective housing that provides solid, stable mechanical support. The protective housing is preferably a lead-line metal structure that also serves as an electrical insulator and thermal cushion for the vacuum chamber 100.

In an X-ray generating system, the electrons pass through the vacuum chamber 100 from a cathode, which is the electron source 300, to the anode, wherein a high voltage is maintained between the cathode and the anode. Generally, the cathode includes a wire filament, typically tungsten, which emits electrons when heated. The temperature of the filament is controlled by a current flow to the filament. More electrons are produced with an increase in the current flowing to the filament. Cathodes that emit electrons by heating a filament are called hot cathodes and can be separated as directly heated cathodes and indirectly heated cathodes. In directly heated cathodes, the filament itself is the cathode and emits the electrons directly. On the other hand, in indirectly heated cathodes, the filament is not the cathode but rather heats a separated cathode consisting of a sheet metal cylinder surrounding the filament, and the cylinder emits electrons. Indirectly heated cathodes are used in most low power vacuum tubes. For example, in most vacuum tubes the cathode is a nickel tube, coated with metal oxides. It is heated by an internal tungsten filament inside, and the heat from the filament causes the outside surface of the oxide coating to emit electrons. The filament of an indirectly heated cathode is usually called the heater.

As described earlier, the electrons emitted from the cathode are directed towards a target anode that initiates the X-ray beam generation process. The system of the present disclosure describes using the dynamic target material 411, which is a liquid, as the target anode. Moreover, the system of the present disclosure utilizes the target material flow system 400 to accommodate the dynamic target material 411. As seen in FIG. 2A, to do so, in addition to the dynamic target material 411 and the pipeline 405, the target material flow system 400 comprises a pump 401, a reservoir 403, and a temperature control unit 409. During the X-ray beam generation process, the dynamic target material 411 needs to be in fluid motion within the pipeline 405 such that a new target area is continuously provided to the electron beam generated at the electron source 300. To do so, the dynamic target material 411, which may be in a solid state within the reservoir 403, is melted via a heating component of the temperature control unit 409 and maintained as a fluid by maintaining a temperature to be above a melting point temperature of the dynamic target material 411. Next, the dynamic target material 411, which is now in a liquid state, is pumped into the pipeline 405 with the pump 401. To do so, the reservoir 403 and the pump 401 are in fluid communication through the pipeline 405. More specifically, the dynamic target material 411 needs to be maintained at a temperature above a melting point temperature. When the electron beam contacts the dynamic target material 411, the temperature of the dynamic target material 411 rises. The temperature of the dynamic target material 411 should be maintained such that the rise in temperature does not damage the thin diamond window assembly 200 and the boundaries between the target material flow system 400 and the vacuum chamber 100.

To ensure that the dynamic target material 411 is maintained above the melting point temperature at a preferred temperature, the reservoir 403, the pump 401, and the pipeline 405 are enclosed by the temperature control unit 409 which can vary from one embodiment to another. Thus, the reservoir 403, the pump 401, and the pipeline 405 are in direct contact with the temperature control unit 409. Further, the dynamic target material 411 serves as a cooling medium for the diamond window 200. The reservoir 403 contains a cooling sub-unit that prevents the liquid medium temperature to rise above the operating temperature range. The cooling sub-unit may be air cooled or water cooled. As seen in FIG. 2B, in a preferred embodiment, the temperature control unit 409 comprises a heating coil that is wrapped around the reservoir 403, the pump 401, and the pipeline 405. The temperature control unit 409 is also used to prevent the system from overheating, especially when a temperature rise occurs when the electron beam strikes the dynamic target material 411. For the dynamic target material 411 to maintain the liquid state, the dynamic target material 411 is in thermal communication with the temperature control unit 409. Preferably, the pump 401 and the pipeline 405 can withstand high temperatures associated with the dynamic target material 411. Moreover, when lead bismuth eutectic is used in a preferred embodiment, the temperature control unit 409 will control the operating temperature of the dynamic target material 411 to be within 100 centigrade (° C.) the melting point of the dynamic target material 411. To further prevent heat related damage, the electron beam is preferably pulsated with a duty factor. Therefore, the thin diamond window assembly 200 is allowed to dissipate heat in between pulses determined by the duty factor. The overall volume of the dynamic target material 411 the reservoir 403 can hold may vary from one embodiment to another. In a preferred embodiment, the reservoir 403 may hold a volume which can be, but is not limited to, a volume within a range of 1 liter (L)-5 L, preferably 2 L-4 L, or about 3 L. In general, the volume of the reservoir 403 needs to be sufficient to circulate within the target material flow system 400 and the temperature control unit 409.

As described earlier, the pump 401 is used to draw a volume of the dynamic target material 411 from the reservoir 403 and inject the dynamic target material 411 into the pipeline 405. In one instance, the pump 401 can inject the dynamic target material 411 into the pipeline 405 with a velocity of 10 meters/sec (m/s). In another instance, the pump 401 can inject the dynamic target material 411 into the pipeline 405 with a velocity of 50 m/s. As described earlier, the pump 401 needs to withstand high temperatures associated with the dynamic target material 411. Failure to do so can result in added maintenance costs, damaged final products, and increased personal hazards. Therefore, when selecting the pump 401 to be used with the dynamic target material 411, the external pump construction and the internal pump construction need to be considered so that the pump 401 can withstand dimensional changes due to thermal expansion. Preferably, the pump 401 used in the system of the present disclosure will comply with ISO 2858 and DIN 24256 standards.

In a preferred embodiment, the temperature control unit 409 is a heating coil that is wrapped around the reservoir 403, the pump 401, and the pipeline 405. The heating coil converts electrical energy into heat through the process of Joule heating, where the passing of an electrical current through a conductor produces heat. In particular, the resistance encountered by the electric current while passing through the conductor produces heat. When the heating coil is being used in a preferred embodiment, the material used in manufacturing the heating coil can be Nichrome, Kanthal, Cupronickel, or Etched foil.

Nichrome, which has 80% nickel and 20% chrome, is preferred due to the relatively high resistance, and forming of an adherent layer of chromium oxide when heated for the first time. The material beneath the adherent layer will not oxidize and will prevent the wire from breaking or burning out.

Kanthal is the trademark for a family of iron-chromium-aluminium (FeCrAl) alloys used in a wide range of resistance and high-temperature applications. Kanthal FeCrAl alloys consist of mainly iron, chromium (20%-30%) and aluminum (4%-7.5%). The alloys are known for their ability to withstand high temperatures and having intermediate electric resistance. As such, it is frequently used in heating elements.

Cupronickel or copper-nickel (CuNi) is an alloy of copper that contains nickel and strengthening elements, such as iron and manganese. The copper content typically varies from 60% to 90%.

Etched foil elements are generally made from the same alloys as resistance wire elements, but are produced with a subtractive photo-etching process that starts with a continuous sheet of metal foil and ends with a complex resistance pattern. These elements are commonly found in precision heating applications like medical diagnostics and aerospace.

As described earlier, the pipeline 405 needs to be manufactured from material that can withstand high temperatures associated with the dynamic target material 411. Furthermore, material compatibility with lead bismuth eutectic also needs to be considered when selecting a material for the pipeline 405. For example, high-nickel-containing materials, such as Stainless Steel-316L and Inconel-693, show an excessive dissolution after staying for 500 or more hours in lead bismuth eutectic at 700° C. Liquid target materials generally have a melting temperature which is generally below 150° C. However, having the capability to withstand temperatures up to 700° C. may be beneficial with liquid target materials that have a higher melting temperature. Due to the high solubility of nickel in liquid lead bismuth eutectic, materials such as stainless steel-316L and Inconel-693 cannot be used in the pipeline 405. On the other hand, aluminum-based alloys may not be used due to their low melting temperature (~660° C.), while titanium and refractory metals may not be used due to their excessive oxidation in the air. Therefore, ferritic steel containing no nickel may be a candidate for manufacturing the pipeline 405. For example, Kanthal may be used due to the availability, absence of nickel, and high content of chromium and aluminum, wherein chromium and aluminum are crucial elements for the formation of protective oxide layers.

In instances where the target material flow system 400 shuts down, and the required temperature is not maintained within the target material flow system 400, the dynamic target material 411 may solidify within the pipeline 405. In order to ensure that the dynamic target material 411 is in liquid state following a shutdown of the target material flow system 40, the system of the present disclosure preferably performs a startup heating process for a predetermined time period. By doing so, the system of the present disclosure ensures that the dynamic target material 411 is in liquid state.

The electrons generated at the electron source 300 collide with the dynamic target material 411 flowing within the target material flow system 400 after passing through a diamond sheet 201 of the thin diamond window assembly 200. The thickness of the diamond sheet 201 is within a range of between 0.01 millimeters (mm) to 0.1 mm, with a preferable thickness that is within a range 0.02 mm to 0.08. The thickness of the diamond window can also be within a range from 0.03 mm to 0.06 mm, 0.04 mm to 0.05 mm. As described earlier, the thin diamond window assembly 200 is positioned within the vacuum chamber 100. Therefore, a front surface of the diamond sheet 201 is exposed to a vacuum environment within the vacuum chamber 100. When integrating the thin diamond window assembly 200 into the target material flow system 400, the diamond sheet 201 is firmly fixed to a pipeline 405 of the target material flow system 400 to prevent leakages of the dynamic target material 411. When integrated, a rear surface of the diamond sheet 201 will undergo a pressure of the dynamic target material 411 flowing through the pipeline 405. In a preferred embodiment, the pressure is within a range of 0.1 Megapascal (MPa)-0.5 MPa with a preferable pressure value of approximately 0.2 MPa. The pressure difference between the front surface and the rear surface may create a bending action on the diamond sheet 201 since the diamond sheet 201 is terminally fixed to the pipeline 405. Thus, the diamond sheet 201 can be considered as a sheet subjected to transverse pressure. The brittleness of diamond along with the tension and compression stresses created from the bending action may cause the diamond sheet 201 to fail. To address the issue, a front metal stiffener 207 and/or a rear metal stiffener 209 are used in the thin diamond window assembly 200. The front metal stiffener 207 and/or the rear metal stiffener 209 are oriented to minimize interaction with the electron beam. The front metal stiffener 207 and the rear metal stiffener 209, which are preferably copper sheets that are attached to the diamond sheet 201, and are used to minimize the overall stress distribution on the diamond sheet 201. The front metal stiffener 207 and the rear metal stiffener 209 will preferably have a thickness within a range of 1 mm-2 mm, with a preferable thickness of 1.5 mm when the diamond sheet 201 has a thickness of approximately 0.03 mm. Even though diamond is used in a preferred embodiment, other materials that can be, but is not limited to, beryllium, tungsten, and molybdenum metal foils may be used in other embodiments of the present disclosure. The thin diamond window assembly 200 must be made of material with high melting temperature.

Figure 17:
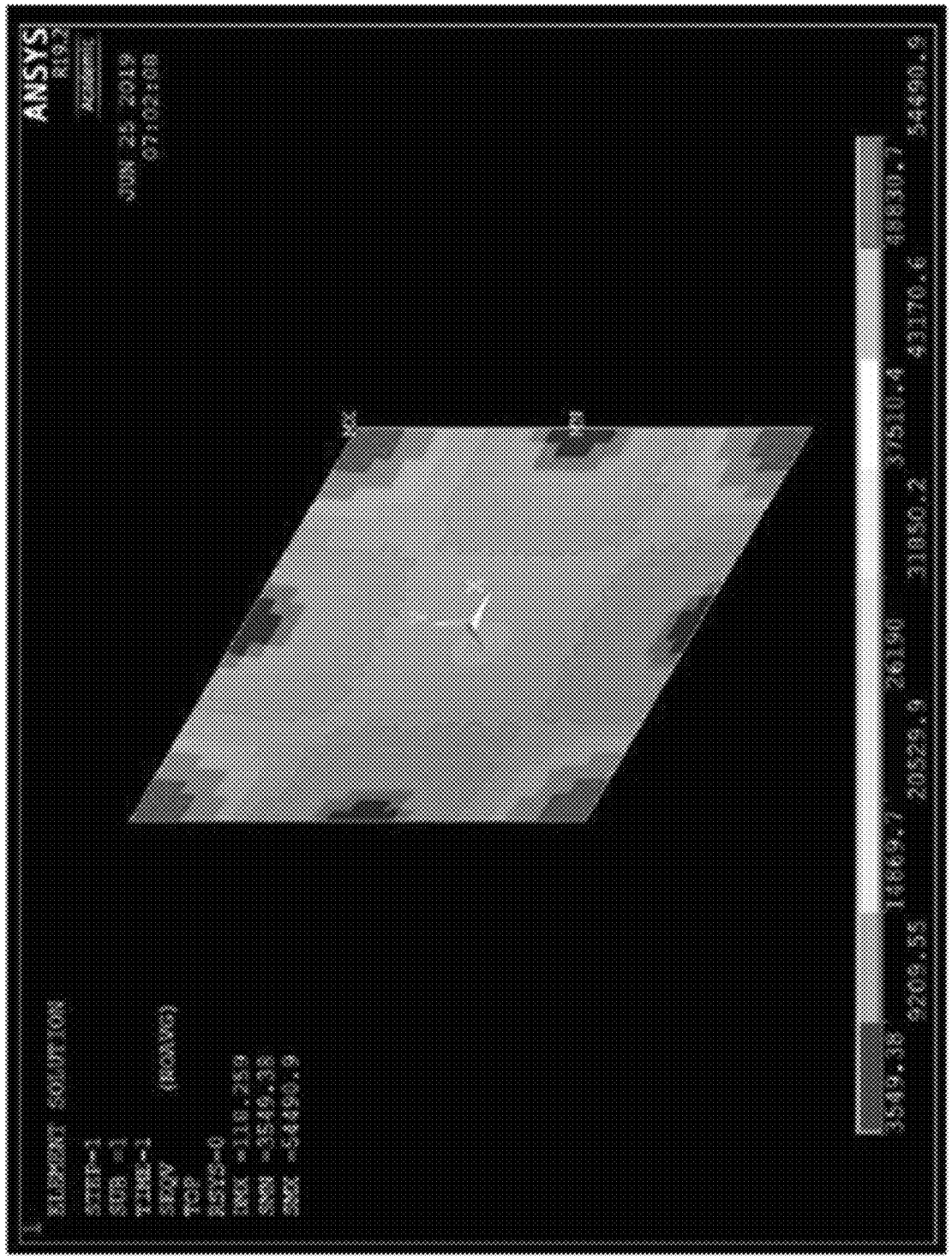
FIG. 17 is an illustration of the Von Mises stress distribution on a diamond sheet with a pressure value of 0.2 megapascal (MPa).

To analyze the stress distribution, the diamond sheet 201 was modelled as a SHELL 181 element type, wherein the SHELL 181 element type is suitable for analyzing thin to moderately-thick shell structures. SHELL 181 is a four-noded element with six degrees of freedom at each node: translations in the x, y, and z directions, and rotations about the x, y, and z axes. The degenerate triangular option should only be used as filler elements in mesh generation. The modulus of elasticity, which is a measure of stiffness, was tested at 1,220,000 MPa (1.2 Gigapascal (GPa) with a Poisson's ratio of 0.2. The boundaries were restricted with zero displacement, wherein $U_x=U_y=U_z=0$, and a pressure of 0.2 MPa was applied on the entire surface area to simulate the pressure applied by the dynamic target material 411 flowing within the pipeline 405. The resulting Von Mises Stress distribution, which is a value used to determine if a material will yield or fracture, is shown in FIG. 17. According to the test results, the minimum stress value is 3.5 GPa and the maximum stress value is 54 GPa. Therefore, with a tensile strength value ranging from 0.8 GPa and 1.2 GPa, diamond will definitely fail.

Figure 18:
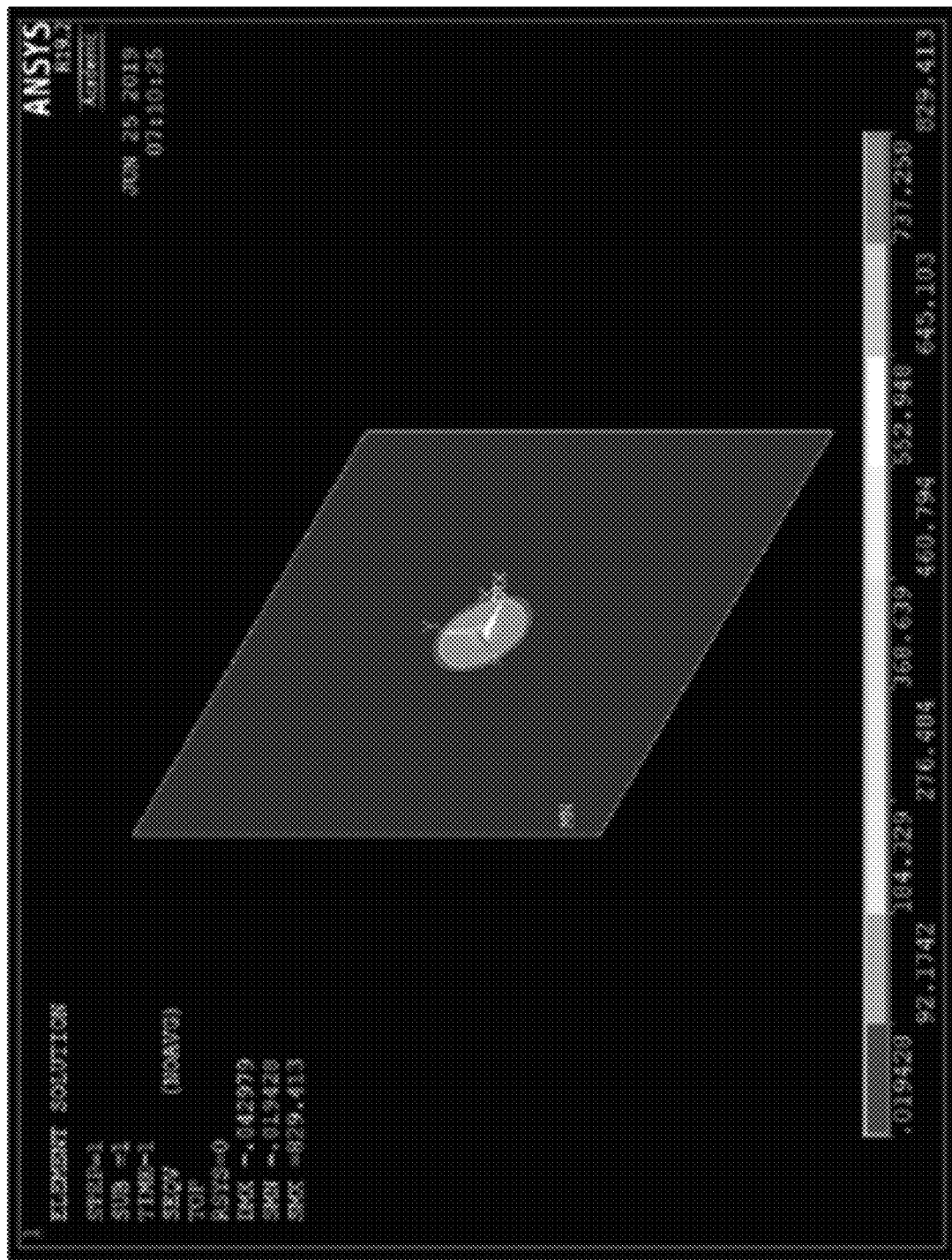
FIG. 18 is an illustration of the Von Mises stress distribution on the diamond sheet with a pressure value of 0.2 MPa when only a circular area with a 5 millimeter (mm) diameter is exposed.

To address the failing of the diamond sheet 201, a majority of the diamond sheet 201 was covered such that only a particular area is exposed to the electron beam from the electron source 300. For testing purposes, when an area with a diameter of 0.5 millimeters (mm) was exposed, as seen in FIG. 18, a maximum stress value of 0.829 GPa was analyzed which is a significant reduction from the 3.5 GPa stress value.

Figure 19:
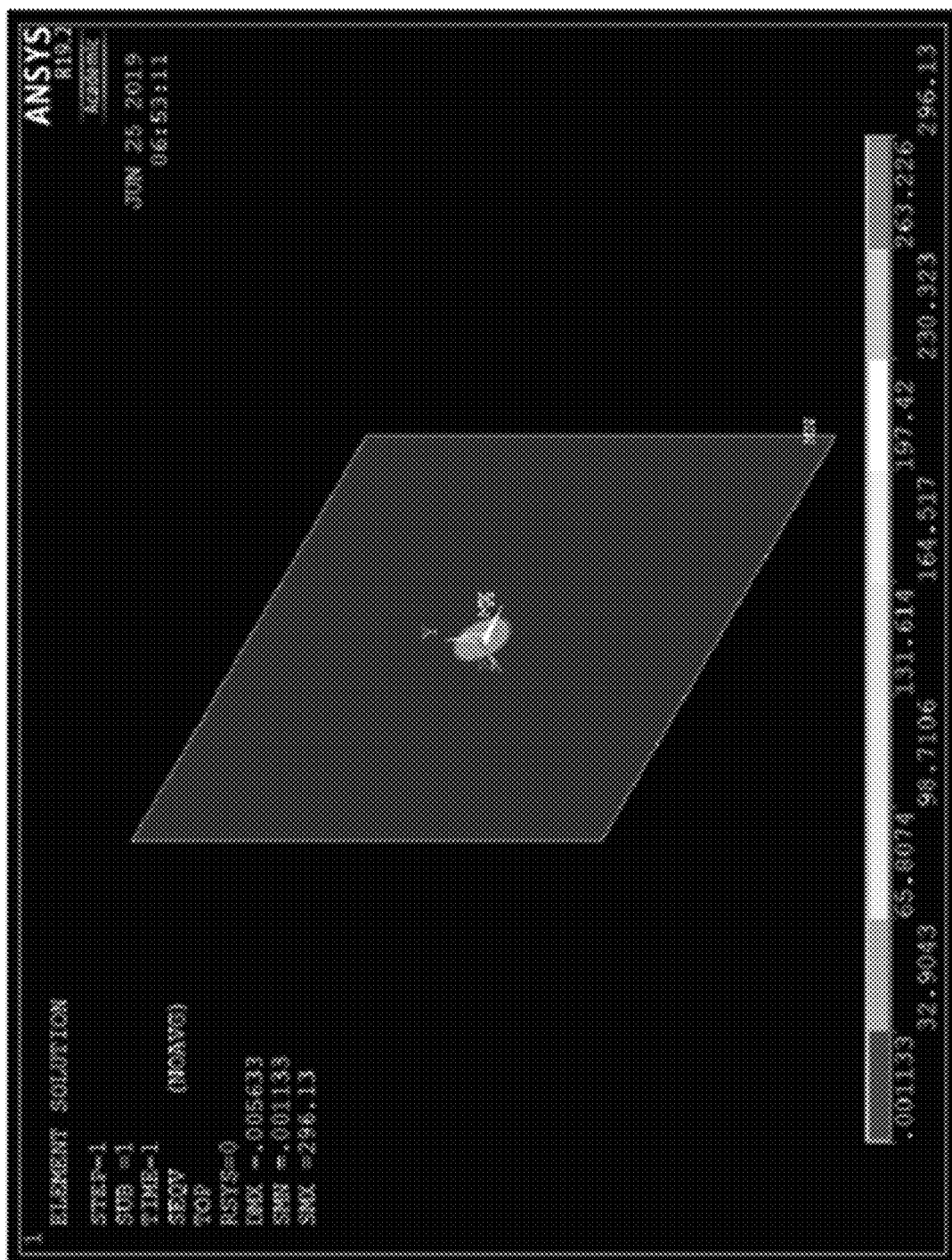
FIG. 19 is an illustration of the Von Mises stress distribution of the diamond window with a pressure value of 0.2 MPa when only a circular area with a 3 mm diameter is exposed.
Figure 20:
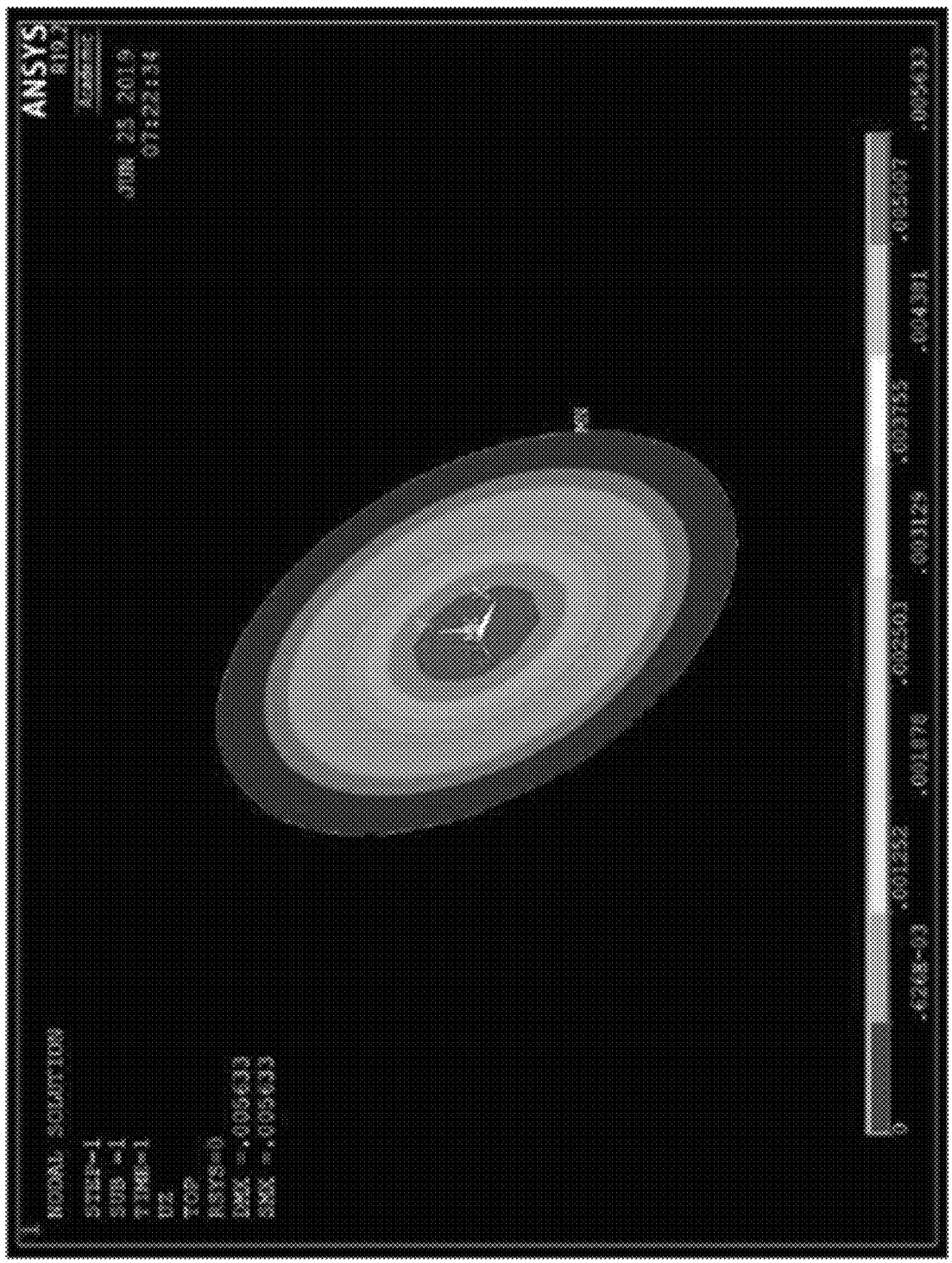
FIG. 20 is an illustration of the displacement of the diamond window in the Z-direction with a pressure value of 0.2 MPa on a circular area with a 3 mm diameter.

As shown in FIG. 19, when an area with a diameter of 0.3 mm was exposed, which still allows the electron beam to pass through and interact with the dynamic target material 411, the maximum stress detected was 0.3 GPa. The 0.3 GPa stress value is less than the failing tensile stress value for diamond, which is 1.2 GPa. The displacement of the diamond sheet 201 when a circular area with a diameter of 3 mm was exposed is shown in FIG. 20, wherein a through thickness displacement of the diamond sheet 201 is approximately 0.05633 mm.

The present disclosure describes using the front metal stiffener 207 and the rear metal stiffener 209, to limit the exposure area of the diamond sheet 201. In a preferred embodiment, to analyze the effects of using copper in the front metal stiffener 207 and the rear metal stiffener 209, a copper sheet is modelled as a SOLID 285 element type with a modulus of elasticity of 121,000 MPa and a Poisson's ratio of 0.34, wherein the modulus of elasticity and Poisson's ratio are temperature dependent. When the copper sheet is modelled as a SOLID 285 element type, the modulus of elasticity and Poisson's ratio are obtained for the operating temperature of the target material flow system 400. Since lead-bismuth eutectic is used, the operating temperature of the target material flow system 400 is the melting temperature of lead-bismuth. Copper, which has a melting temperature around 1000° C., is selected due to the melting temperature which is high compared to the dynamic target material 411 that has a low melting temperature and a high atomic number. In another embodiment, if the dynamic target material 411 has a high melting temperature, the stiffeners used in the thin diamond window assembly 200 will be manufactured from a different material. As an alternative to using a different material for the stiffeners, the calculations of the stresses and displacements may be revised using values of modulus of elasticity and Poisson's ratio at the desired operating temperature, which is the melting temperature of the dynamic target material.

Figure 21:
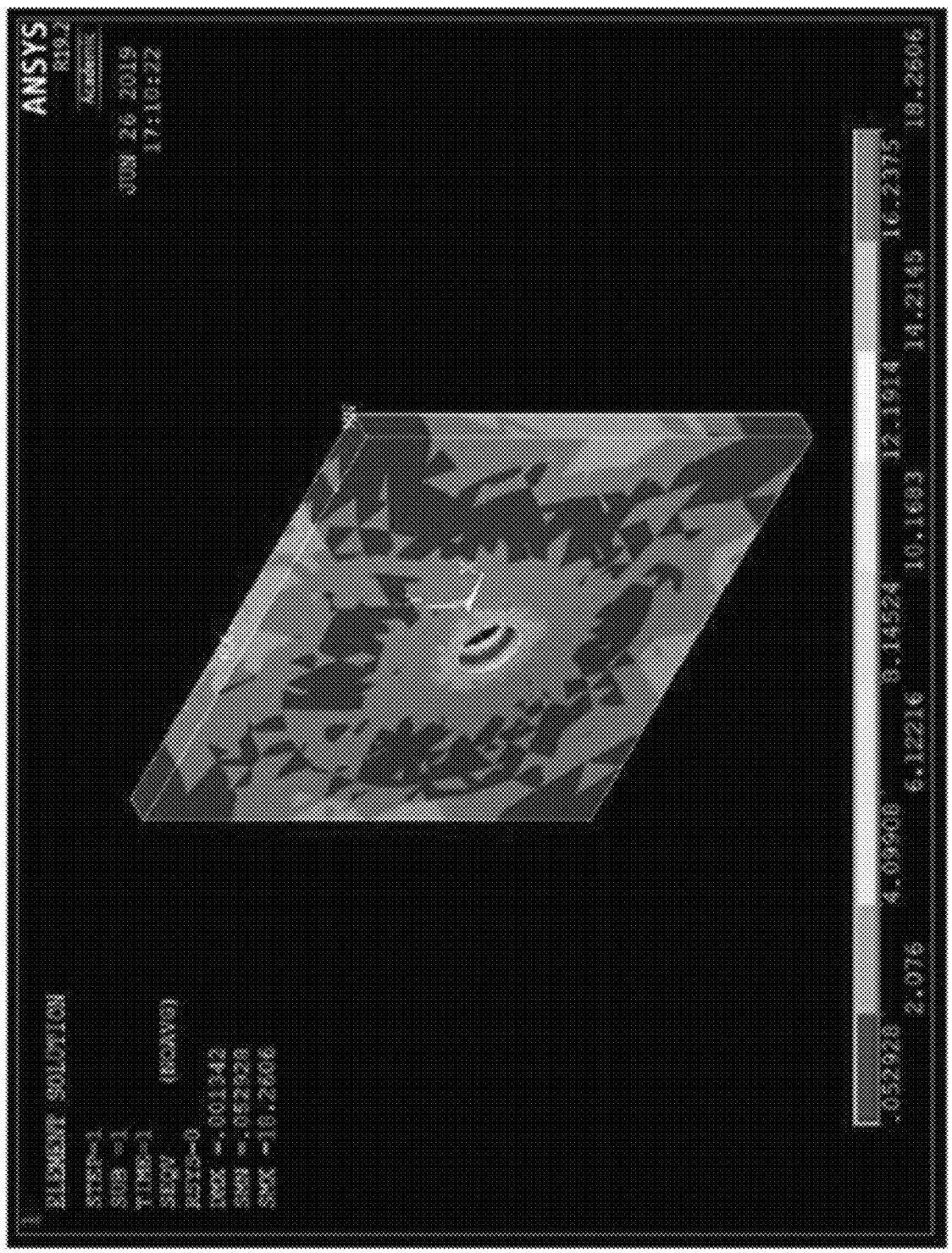
FIG. 21 is an illustration of the Von Mises stress distribution of a copper sheet with a pressure of 0.2 MPa.
Figure 22:
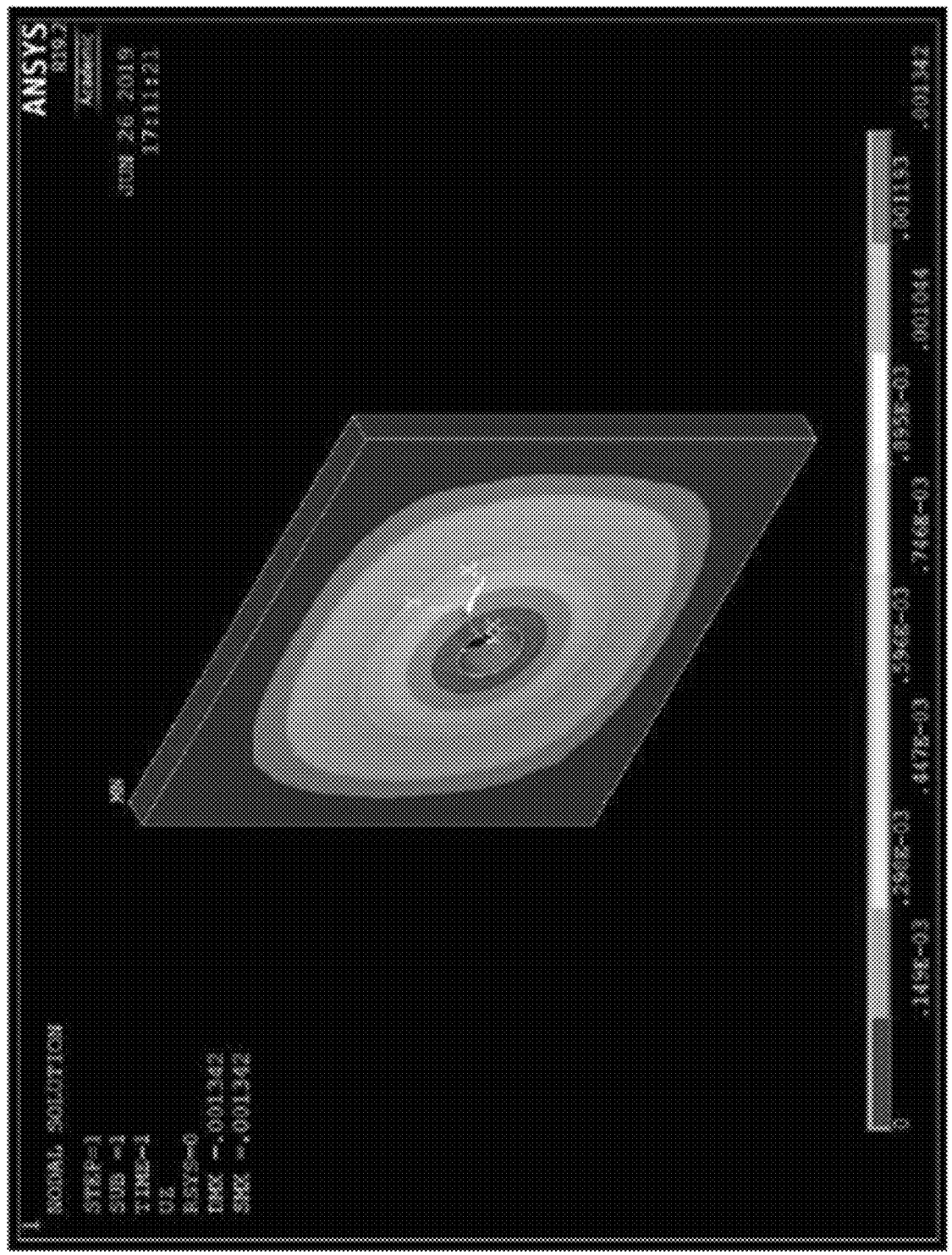
FIG. 22 is an illustration of the displacement of the copper sheet in the Z-direction with a pressure value of 0.2 MPa on a circular area with a 3 mm diameter.

In a preferred embodiment, a copper sheet having a thickness of 1.5 mm and having a width and length matching the diamond sheet 201 is used. The Von Mises stress distribution on the copper sheet when 0.21 MPa is applied is shown in FIG. 21. The displacement of the copper sheet in the Z-direction is shown in FIG. 22. The stress distribution and the displacement of the copper sheet is relatively small when compared to the stress distribution and the displacement of the diamond sheet 201.

According to the tests, the maximum displacement of the copper sheets (0.01 mm) in the Z-direction is considerably smaller than the maximum displacement of the diamond sheet 201 (0.05 mm). Thus, if the displacement of the diamond sheet 201 is governed by the displacement of the copper sheet, the maximum displacement will not be greater than the displacement of copper. As a result, the diamond sheet 201 will not fail.

Figure 4:
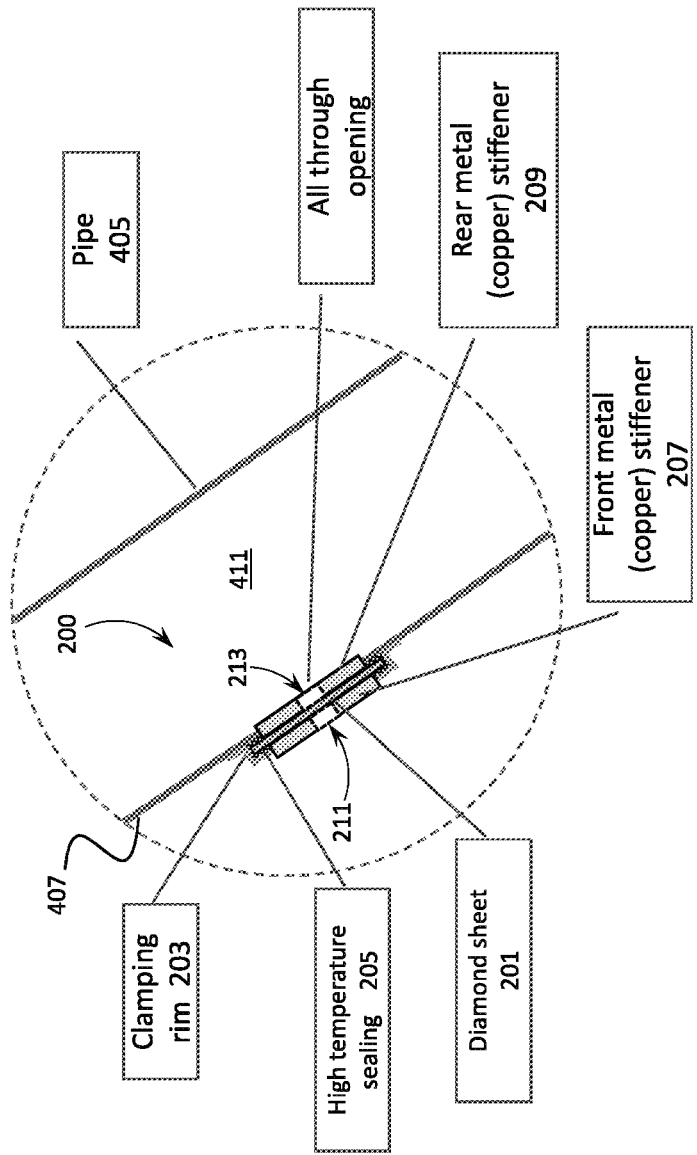
FIG. 4 is a detailed view of the thin diamond window assembly of the present disclosure, wherein the thin diamond window assembly includes a front metal stiffener, a rear metal stiffener, a front opening, and a rear opening, wherein the rear metal stiffener traverses an external surface of the pipeline.

As seen in FIG. 4, in one embodiment, the thin diamond window assembly 200 comprises a clamping rim 203, a high temperature sealing 205, a diamond sheet 201, a front metal stiffener 207, a rear metal stiffener 209, a front opening 211 and a rear opening 213. The front metal stiffener 207 and the rear metal stiffener 209 are used to isolate a target area on the diamond sheet 201 for the electron beam to collide with and generate X-rays. To do so, the diamond sheet 201 is positioned in between the front metal stiffener 207 and the rear metal stiffener 209. The front opening 211 and the rear opening 213 are used to guide the electron beam towards the dynamic target material 411. In order to do so, the front opening 211 centrally traverses the front metal stiffener 207, and the rear opening 213 centrally traverses the rear metal stiffener 209. Thus, by aligning the front opening 211 and the rear opening 213 a beam channel is configured for the electron beam to pass through the diamond sheet 201 and collide with the dynamic target material 411. When integrating the thin diamond window assembly 200 into the target material flow system 400, the rear metal stiffener 209 traverses into an external surface 407 of the pipeline 405. To secure the thin diamond window assembly 200, the front metal stiffener 207, the diamond sheet 201, and the rear metal stiffener 209 are attached to the external surface 407 of the pipeline 405 with the high temperature sealing 205 and the clamping rim 203.

Figure 5A:
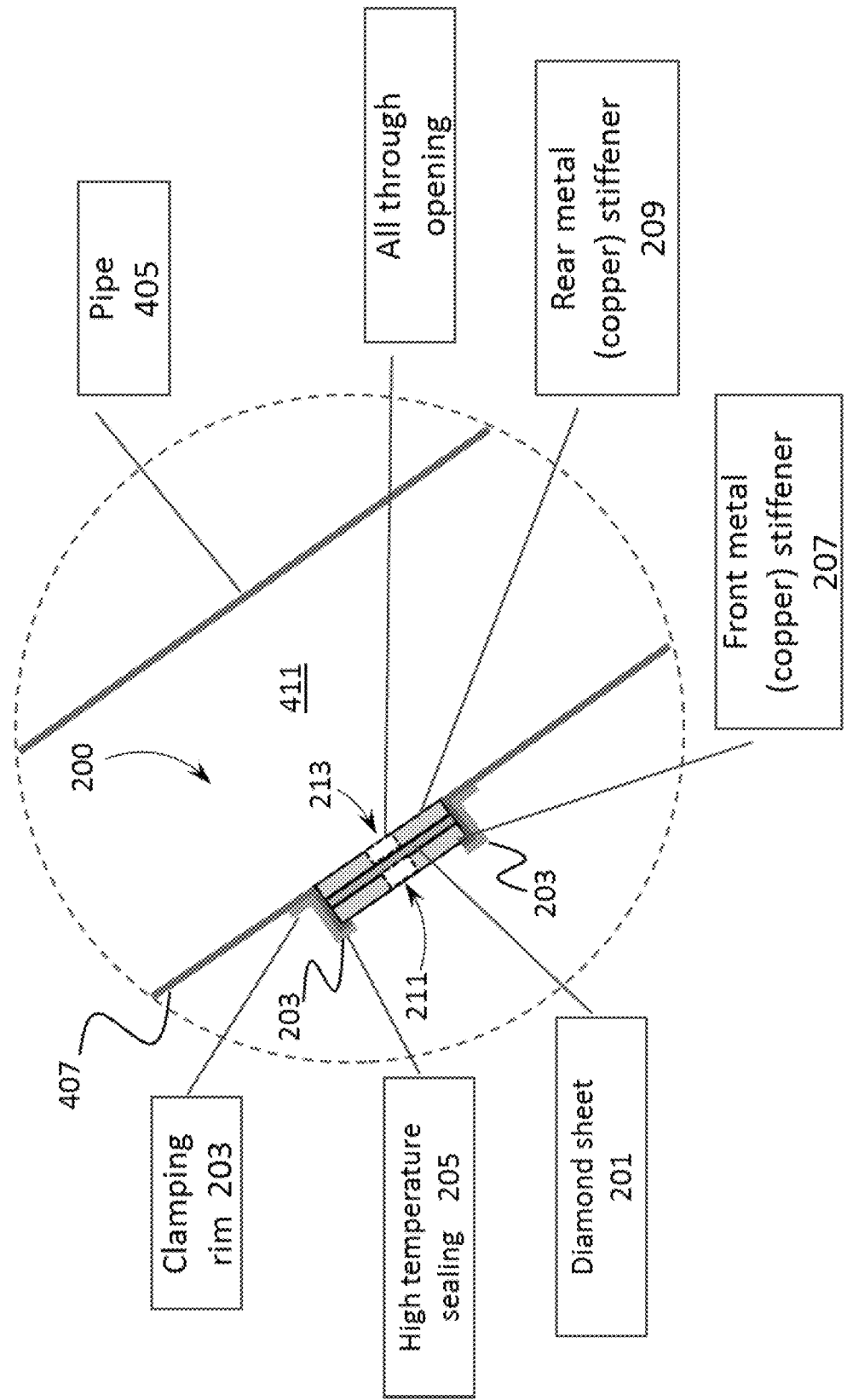
FIG. 5A is a detailed view of the thin diamond window assembly of the present disclosure, wherein the thin diamond window assembly includes a front metal stiffener, a rear metal stiffener, a front opening, and a rear opening that are pressed against an external surface of the pipeline with a clamping rim and a high temperature sealing, wherein the rear metal stiffener is positioned along the external surface of the pipeline.
Figure 5B:
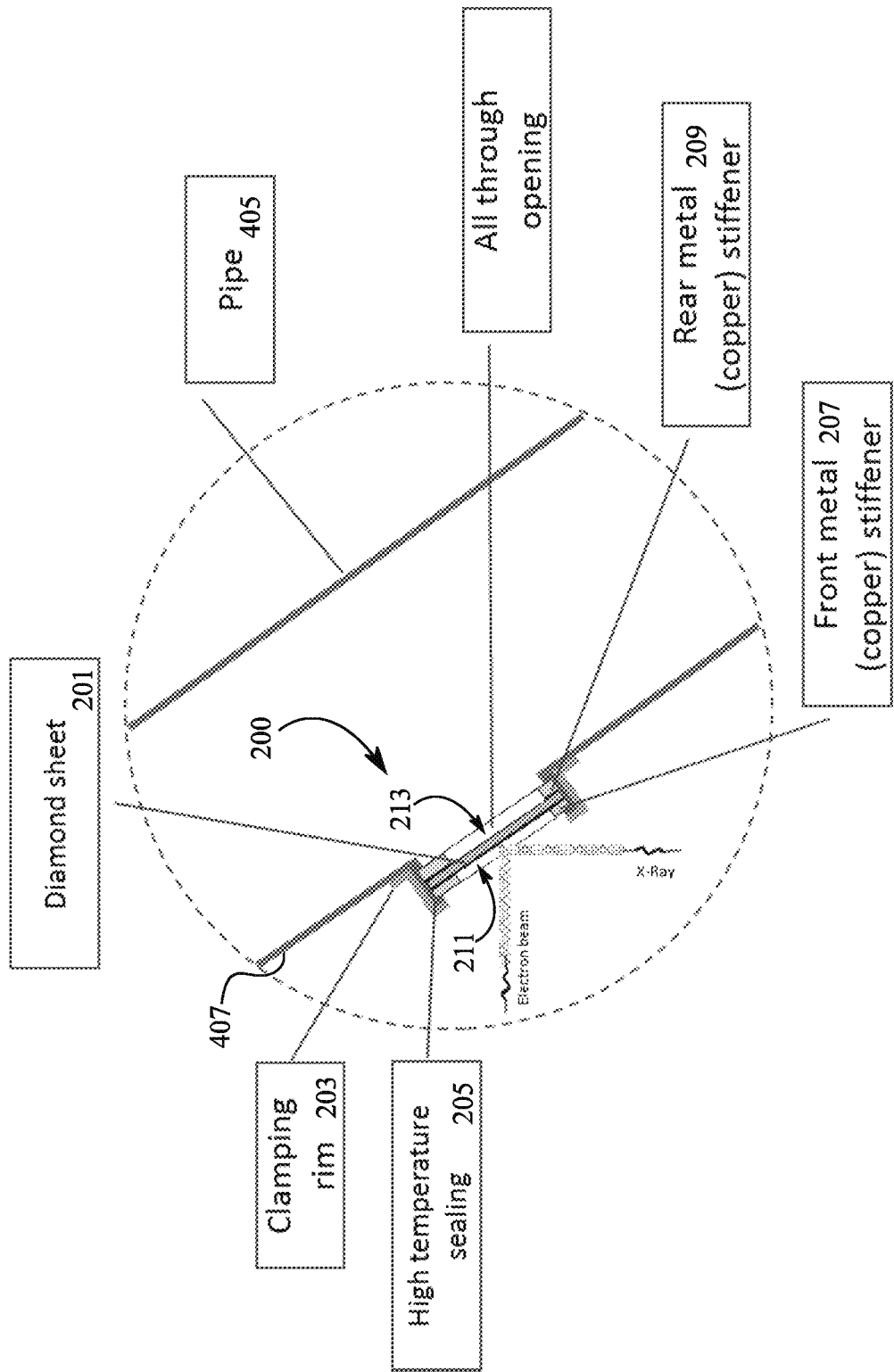
FIG. 5B is a detailed view of the thin diamond window assembly of the present disclosure illustrating the arrival of the electron beam and the projection of the X-rays, wherein the thin diamond window assembly includes a front metal stiffener, a rear metal stiffener, a front opening, and a rear opening that are pressed against an external surface of the pipeline with a clamping rim and a high temperature sealing, wherein the rear metal stiffener is positioned along the external surface of the pipeline.
Figure 10:
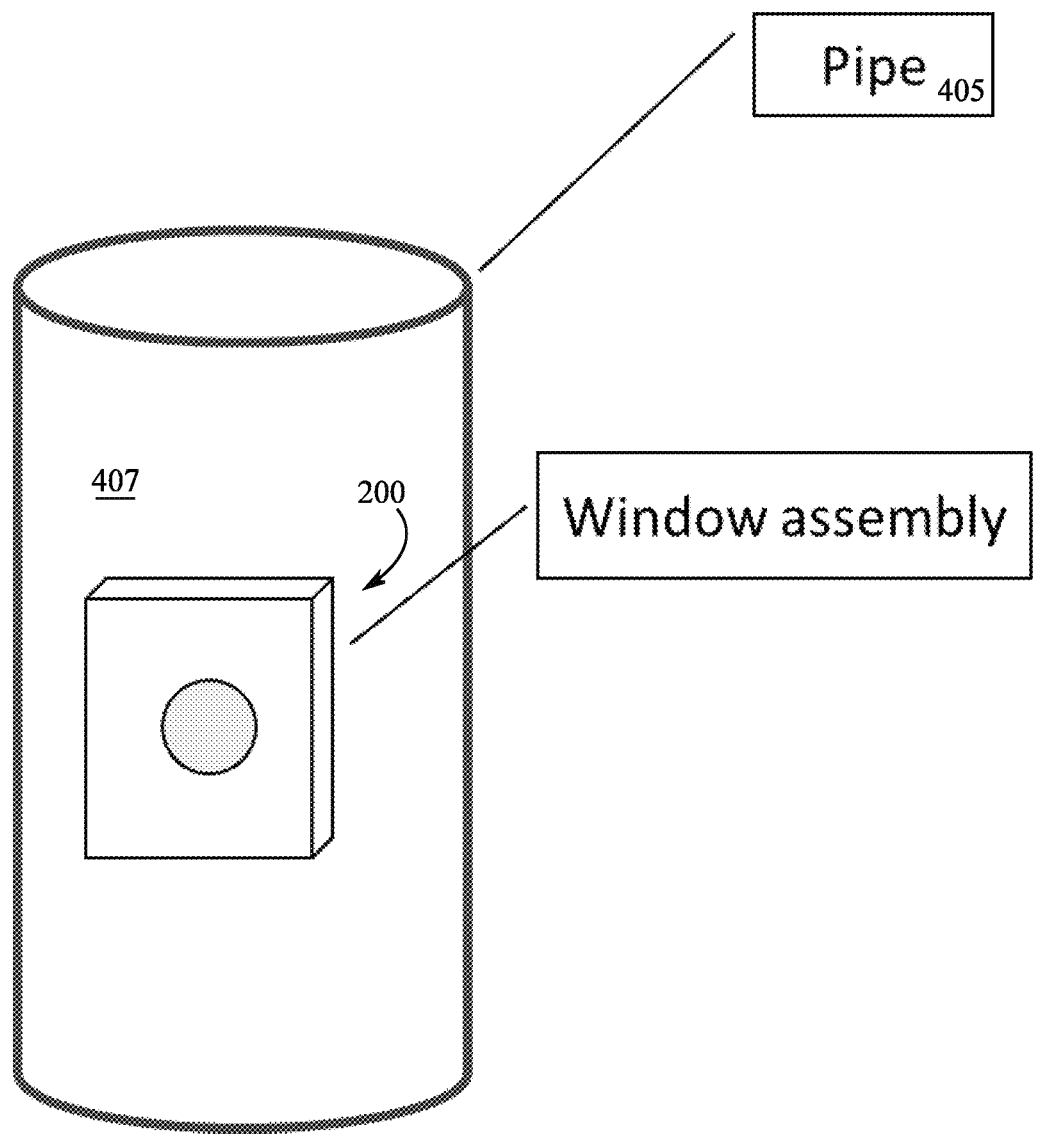
FIG. 10 is a perspective view illustrating the thin diamond window assembly attached to the external surface of the pipeline.

As seen in FIG. 5A and FIG. 5B, in another embodiment, the thin diamond window assembly 200 comprises a clamping rim 203, a high temperature sealing 205, a diamond sheet 201, a rear metal stiffener 209, and a rear opening 213. The diamond sheet 201 is attached to the rear metal stiffener 209 opposite the pipeline 405 and is positioned in between the front metal stiffener 207 and the rear metal stiffener 209. The front opening 211 centrally traverses the front metal stiffener 207. The rear opening 213 centrally traverses into the rear metal stiffener 209 allowing the electron beam to pass through the diamond sheet 201. When the thin diamond window assembly 200 is integrated into the target material flow system 400, the rear metal stiffener 209 is positioned along an external surface 407 of the pipeline 405, and front metal stiffener 207 and the diamond sheet 201 are secured against the external surface 407 of the pipeline 405, as seen in FIG. 10, with the high temperature sealing 205 and the clamping rim 203.

Figure 6:
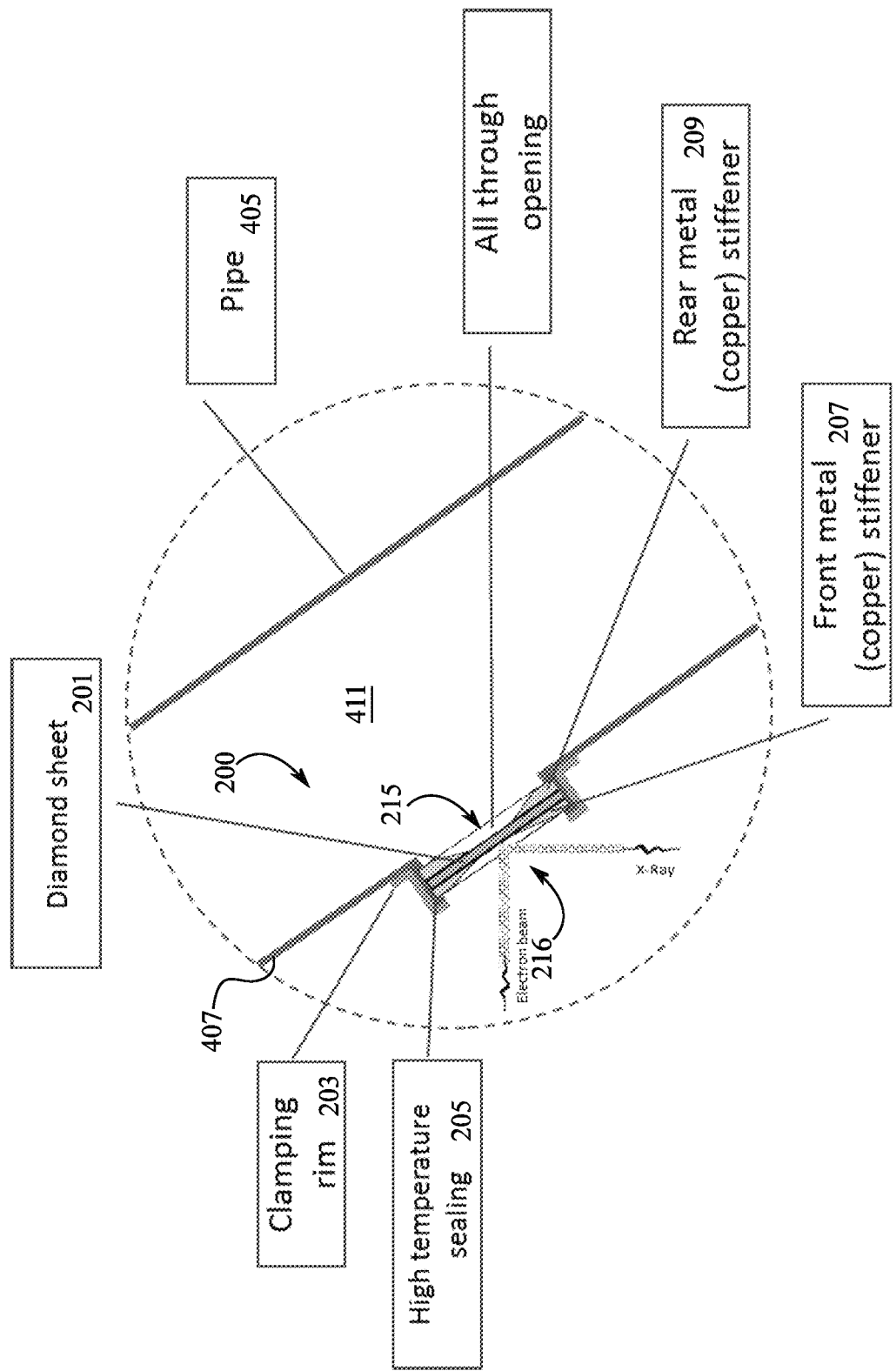
FIG. 6 is a detailed view of the thin diamond window assembly of the present disclosure, wherein the thin diamond window assembly includes a front metal stiffener, a rear metal stiffener, a front countersink hole, a rear countersink hole that are pressed against an external surface of the pipeline with a clamping rim and a high temperature sealing, wherein the rear metal stiffener is positioned along the surface of the pipeline.

As seen in FIG. 6, in another embodiment, the thin diamond window assembly 200 comprises a clamping rim 203, a high temperature sealing 205, a diamond sheet 201, a front metal stiffener 207, a rear metal stiffener 209, a front countersink hole 216, and a rear countersink hole 215. As described earlier, the front metal stiffener 207 and the rear metal stiffener 209 are used to isolate a target area on the diamond sheet 201 for the electron beam to collide with dynamic target material 411 and generate X-rays. To do so, the diamond sheet 201 is positioned in between the front metal stiffener 207 and the rear metal stiffener 209. The front countersink hole 216 and the rear countersink hole 215 are used to allow the electron beam to travel towards the dynamic target material 411. In order to do so, the front countersink hole 216 centrally traverses the front metal stiffener 207, and the rear countersink hole 215 centrally traverses the rear metal stiffener 209. Thus, by aligning the front countersink hole 216 and the rear countersink hole 215 a beam channel is configured for the electron beam to pass through the diamond sheet 201 and collide with the dynamic target material 411. In particular, the purpose of using the front countersink hole 216 and the rear countersink hole 215 is to ensure that the electron beam has sufficient space to pass through to the dynamic target material 411 without colliding with the front metal stiffener 207 or the rear metal stiffener 209. When integrating the thin diamond window assembly 200 into the target material flow system 400, the rear metal stiffener 209 is positioned along the external surface 407 of the pipeline 405. To secure the thin diamond window assembly 200 against the pipeline 405, the front metal stiffener 207, the diamond sheet 201, and the rear metal stiffener 209 are pressed against the external surface 407 with the high temperature sealing 205 and the clamping rim 203.

Figure 7:
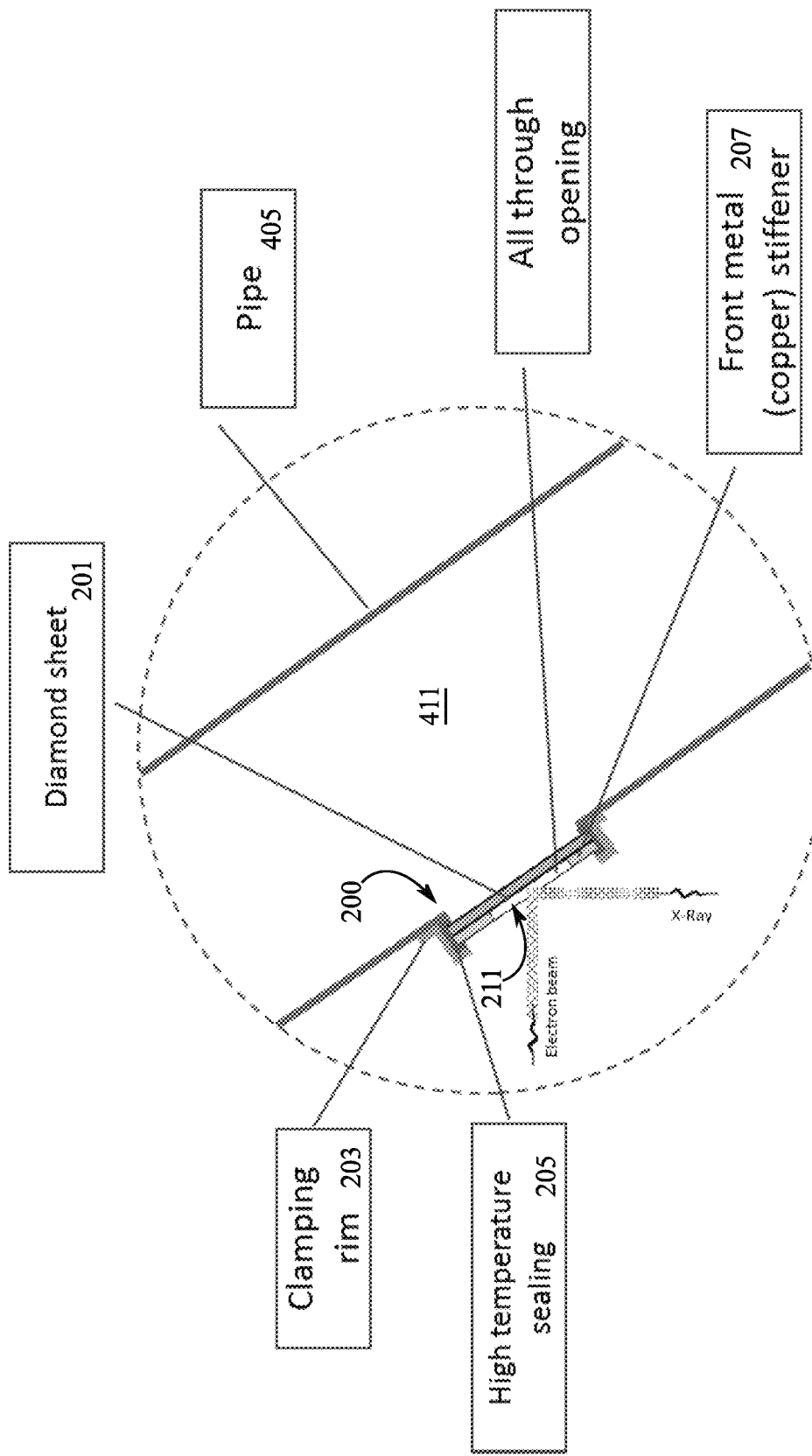
FIG. 7 is a detailed view of the thin diamond window assembly of the present disclosure, wherein the thin diamond window assembly includes a diamond sheet, a front metal stiffener and a front opening, wherein the diamond sheet and the front metal stiffener are pressed against the external surface of the pipeline with a clamping rim.

As seen in FIG. 7, in another embodiment, the thin diamond window assembly 200 comprises a clamping rim 203, a high temperature sealing 205, a diamond sheet 201, a front metal stiffener 207, and a front opening 211. The diamond sheet 201 is attached to the front metal stiffener 207, and is positioned in between the pipeline 405 and the front metal stiffener 207. The front opening 211 centrally traverses into the front metal stiffener 207 allowing the electron beam to pass through the diamond sheet 201. In addition to allowing the electron beam to pass through and collide with the dynamic target material 411, the front metal stiffener 207 stiffens the diamond sheet 201 against the pressure gradient from the dynamic target material 411, which contains a high pressure compared to the vacuum chamber 100, which is at a lower pressure. Thus, any deforming that may occur in the diamond sheet 201 may be prevented. When the thin diamond window assembly 200 is integrated into the target material flow system 400, the diamond sheet 201 is pressed against the external surface 407 of the pipeline 405. To secure the diamond sheet 201 against the pipeline 405, the front metal stiffener 207 and the diamond sheet 201 are pressed against the external surface 407 with the high temperature sealing 205 and the clamping rim 203.

Figure 8A:
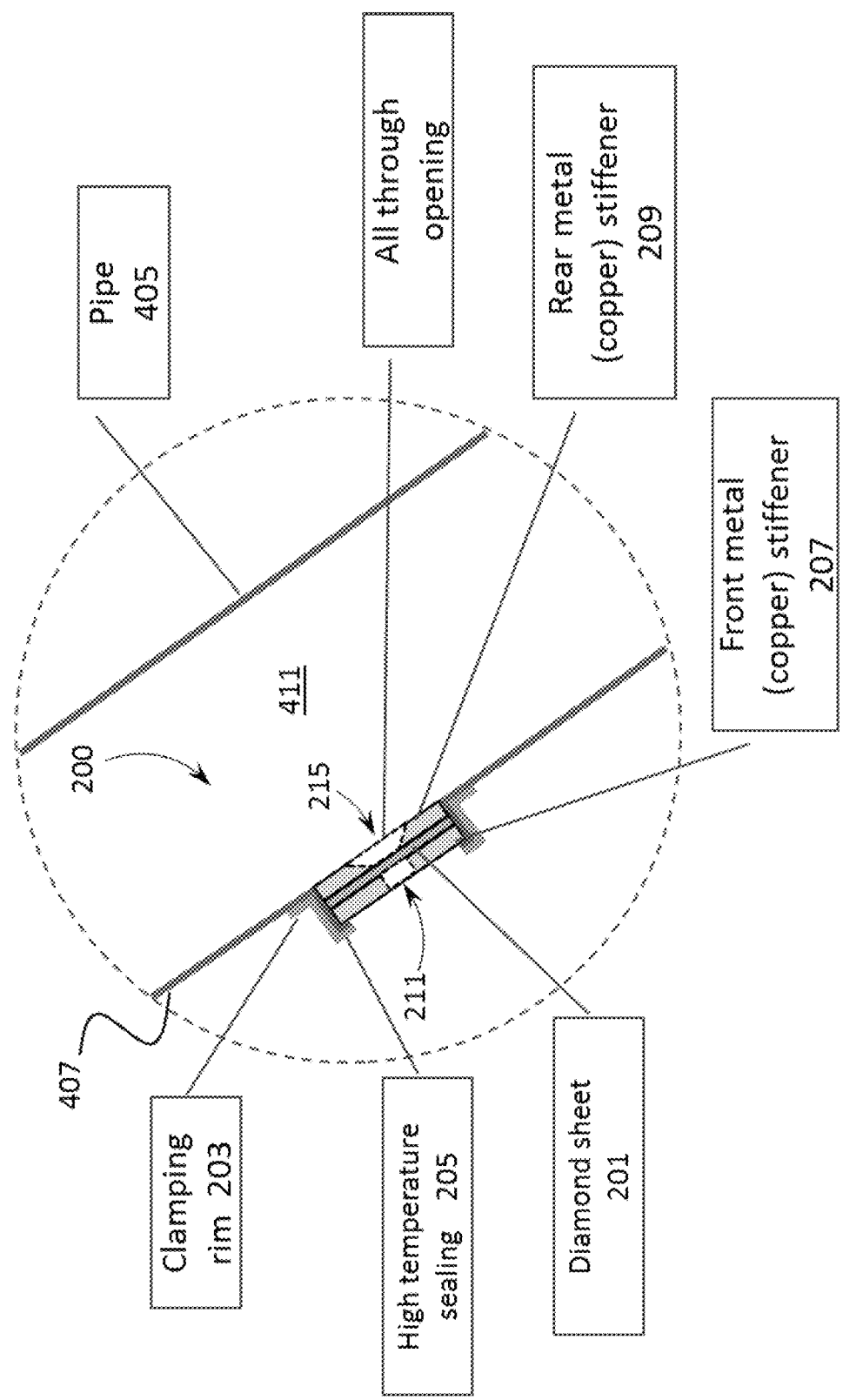
FIG. 8A is a detailed view of the thin diamond window assembly of the present disclosure, wherein the thin diamond window assembly includes a front metal stiffener, a rear metal stiffener, a front opening, and a rear countersink hole that are pressed against an external surface of the pipeline with a clamping rim and a high temperature sealing, wherein the rear metal stiffener is positioned along the external surface of the pipeline.
Figure 23:
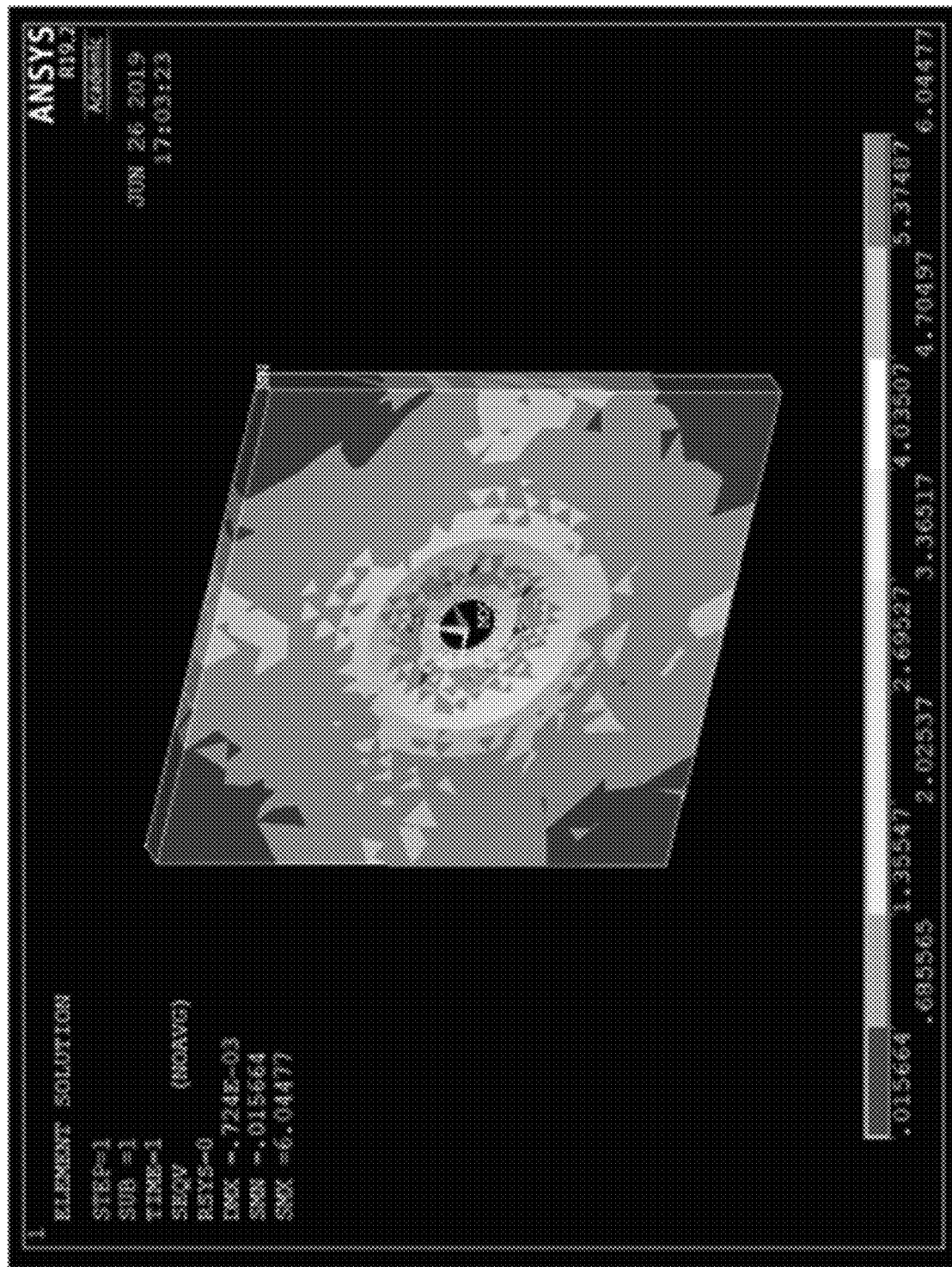
FIG. 23 is an illustration of the Von Mises stress distribution of a copper plate with a cut-through frustum and applied pressure of 0.2 MPa.
Figure 24:
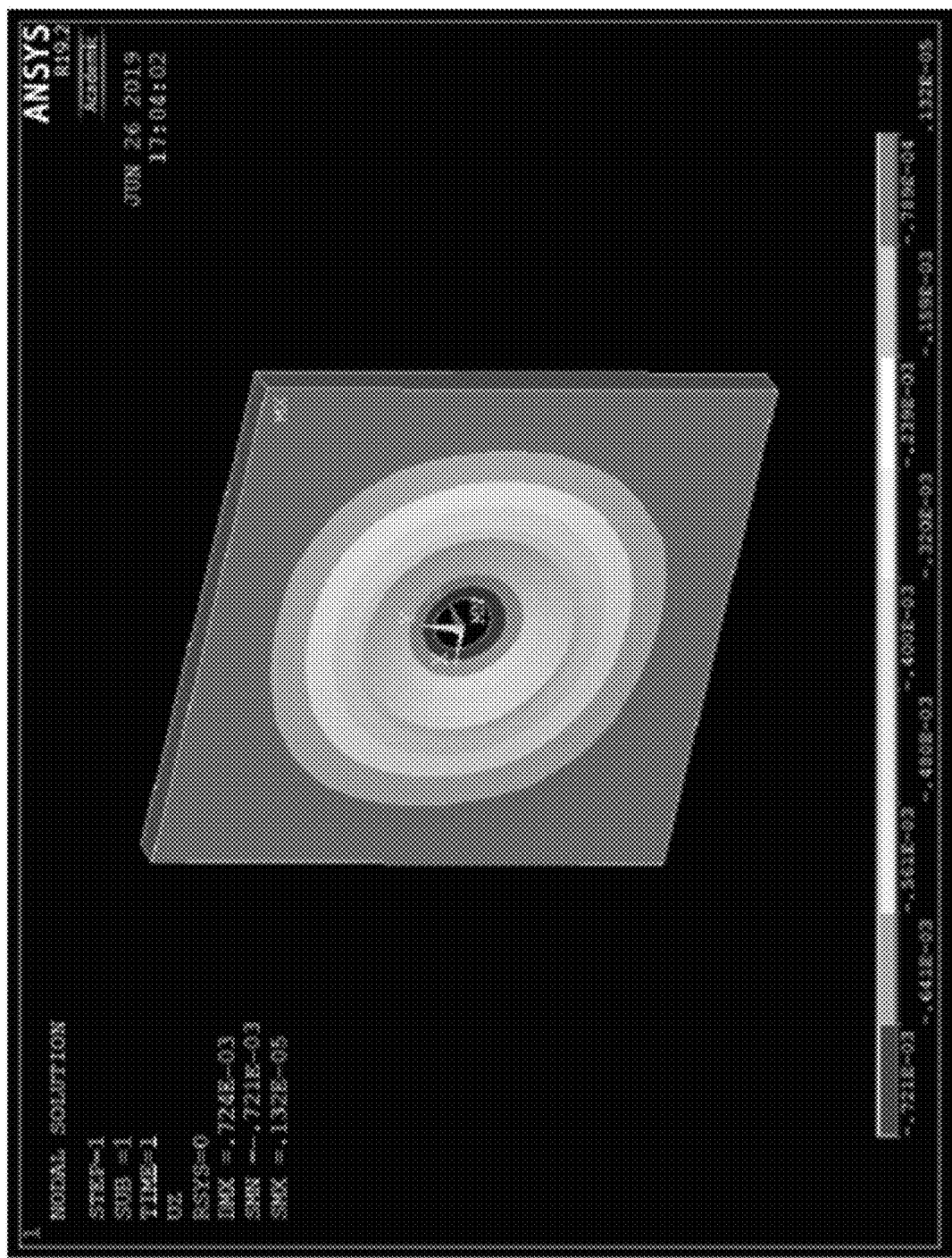
FIG. 24 is an illustration of the displacement of the copper sheet with a cut-through frustum in the Z-direction with a pressure value of 0.2 MPa on a circular area with a 3 mm diameter.

As seen in FIG. 8A, in another embodiment, the thin diamond window assembly 200 comprises a clamping rim 203, a high temperature sealing 205, a diamond sheet 201, a front metal stiffener 207, a rear metal stiffener 209, a front opening 211 and a rear countersink hole 215. Since the dynamic target material 411 flow may be affected by the rear opening 213 which perpendicularly traverses into the rear metal stiffener 209, the use of the rear countersink hole 215 may be beneficial by providing an effective geometry enabling fluid flow. The effectiveness on the stress distribution was measured for a rear countersink hole 215 having a first lateral base with a diameter within a range of 2 mm-6 mm and a second lateral base with a diameter within a range of 8 mm-12 mm. Preferably, the first lateral base has a diameter of 3 mm and a second lateral base has a diameter of 10 mm. When a pressure of 0.2 MPa is applied, the Von Mises stress distribution and the displacement in the Z-direction is shown in FIG. 23 and FIG. 24 respectively. The test results show that the copper sheet can withstand the pressure even with the use of the rear countersink hole 215. The stress analysis tests conducted for both the diamond sheet 201 and the copper sheet were linear elastic. If the diamond sheet 201 is sandwiched in between two copper sheets, the deformation of the diamond sheet 201 will be governed by the copper sheets.

Similar to previous instances, the front metal stiffener 207 and the rear metal stiffener 209 are used to isolate a target area on the diamond sheet 201 for the electron beam to pass through and generate X-rays by colliding with the dynamic target material 411. To do so, the diamond sheet 201 is positioned in between the front metal stiffener 207 and the rear metal stiffener 209. The front opening 211 and the rear countersink hole 215 are used to guide the electron beam towards the dynamic target material 411. In order to do so, the front opening 211 centrally traverses the front metal stiffener 207 and the rear countersink hole 215 centrally traverses the rear metal stiffener 209. Thus, by aligning the front opening 211 and the rear countersink hole 215 a beam channel is configured for the electron beam to pass through the diamond sheet 201 and collide with the dynamic target material 411. When integrating the thin diamond window assembly 200 into the target material flow system 400, the rear metal stiffener 209 is positioned along the external surface 407 of the pipeline 405. To secure the thin diamond window assembly 200 against the pipeline 405, the front metal stiffener 207, the diamond sheet 201, and the rear metal stiffener 209 are pressed against the external surface 407 with the high temperature sealing 205 and the clamping rim 203.

Figure 8B:
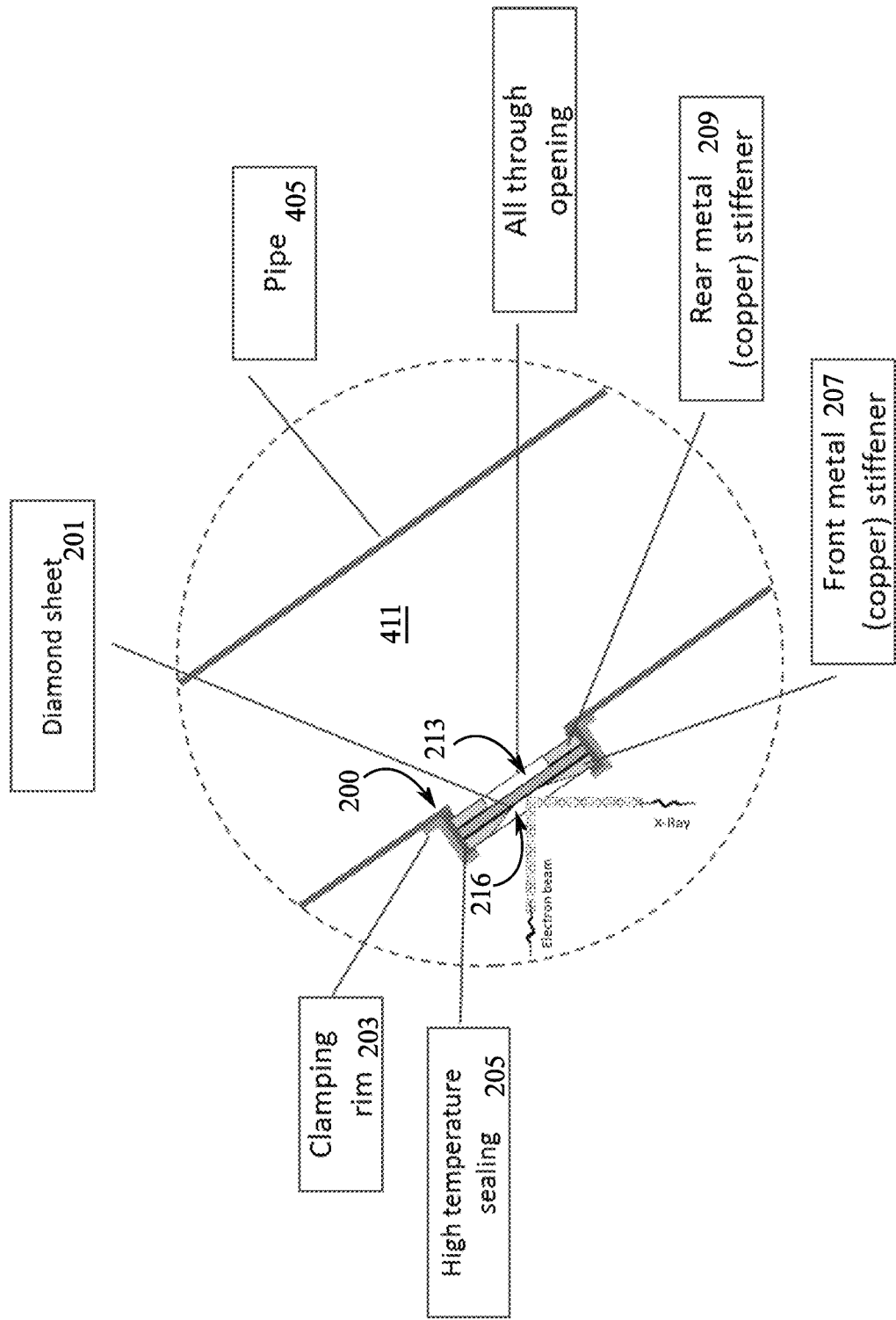
FIG. 8B is a detailed view of the thin diamond window assembly of the present disclosure, wherein the thin diamond window assembly includes a front metal stiffener, a rear metal stiffener, a front countersink hole, and a rear countersink hole that are pressed against an external surface of the pipeline with a clamping rim and a high temperature sealing, wherein the rear metal stiffener is positioned along the external surface of the pipeline.

Similar to the embodiment illustrated in FIG. 8A, as seen in FIG. 8B, in another embodiment, the thin diamond window assembly 200 comprises a clamping rim 203, a high temperature sealing 205, a diamond sheet 201, a front metal stiffener 207, a rear metal stiffener 209, a front countersink hole 216, and a rear opening 213. The front metal stiffener 207 and the rear metal stiffener 209 are used to isolate a target area on the diamond sheet 201 for the electron beam to collide with and generate X-rays. To do so, the diamond sheet 201 is positioned in between the front metal stiffener 207 and the rear metal stiffener 209. The front countersink hole 216 and the rear opening 213 are used to guide the electron beam towards the dynamic target material 411. In order to do so, the front countersink hole 216 centrally traverses the front metal stiffener 207 and rear opening 213 centrally traverses the rear metal stiffener 209. Thus, by aligning the front countersink hole 216 and the rear opening 213 a beam channel is configured for the electron beam to pass through the diamond sheet 201 and collide with the dynamic target material 411. When integrating the thin diamond window assembly 200 into the target material flow system 400, the rear metal stiffener 209 is positioned along the external surface 407 of the pipeline 405. To secure the thin diamond window assembly 200 against the pipeline 405, the front metal stiffener 207, the diamond sheet 201, and the rear metal stiffener 209 are pressed against the external surface 407 with the high temperature sealing 205 and the clamping rim 203.

Figure 9:
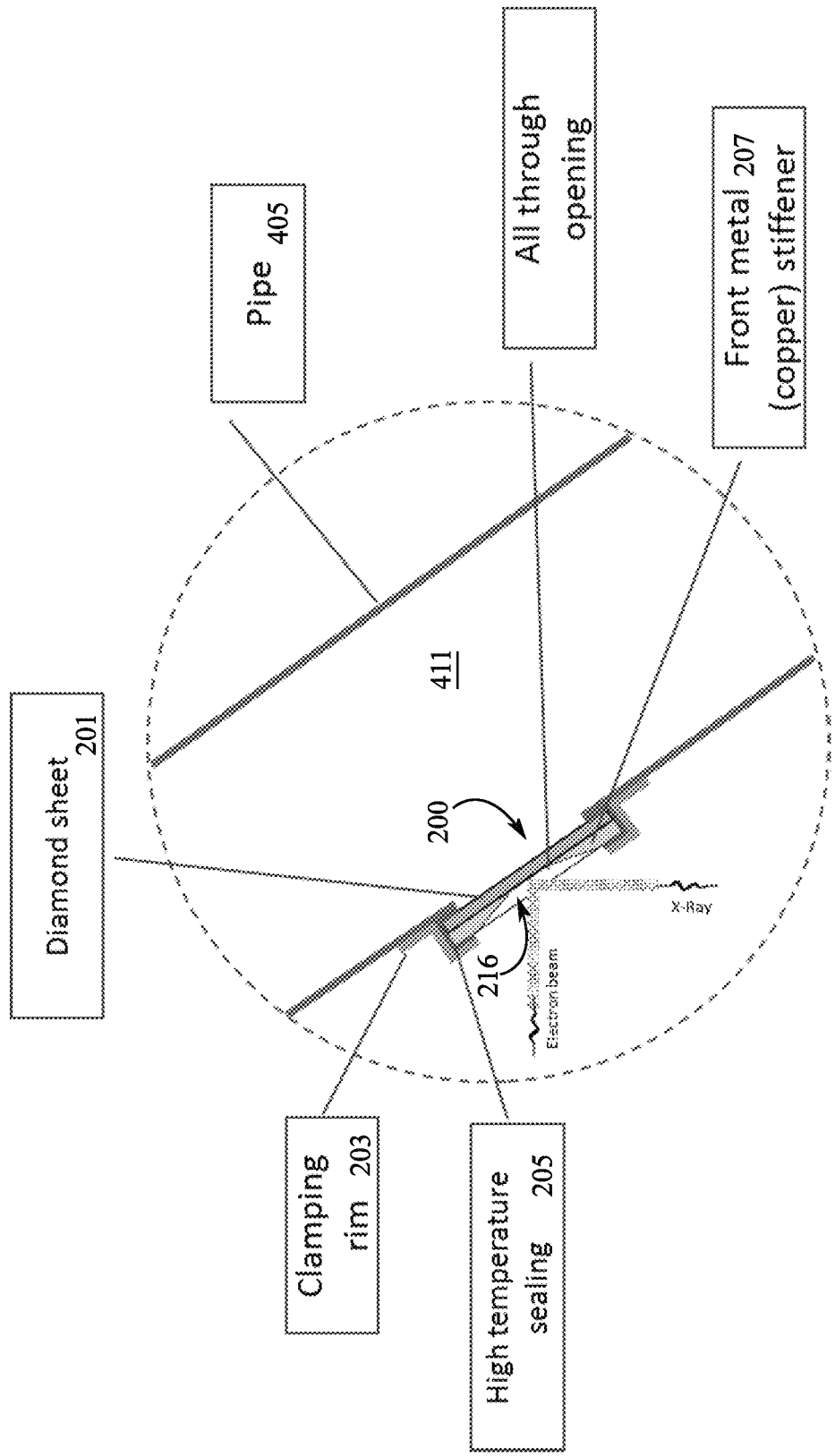
FIG. 9 is a detailed view of the thin diamond window assembly of the present disclosure, wherein the thin diamond window assembly includes a diamond sheet, a front metal stiffener, and a front countersink hole, wherein the diamond sheet is pressed against the external surface of the pipeline with a clamping rim.

As seen in FIG. 9, in another embodiment, the thin diamond window assembly 200 comprises a clamping rim 203, a high temperature sealing 205, a diamond sheet 201, a front metal stiffener 207, and a front countersink hole 216. The diamond sheet 201 is attached to the front metal stiffener 207. The front countersink hole 216 centrally traverses into the front metal stiffener 207 allowing the electron beam to pass through the diamond sheet 201. When the thin diamond window assembly 200 is integrated into the target material flow system 400, the diamond sheet 201 is positioned along the external surface 407 of the pipeline 405 and is positioned in between the front metal stiffener 207 and the external surface 407 of the pipeline 405. To secure the thin diamond window assembly 200 against the pipeline 405, the front metal stiffener 207 and the diamond sheet 201 are pressed against the external surface 407 with the high temperature sealing 205 and the clamping rim 203.

Diamond is used for the electron beam window due to properties such as the ability to withstand high temperatures from both the impact of electrons and the dynamic target material 411. In a preferred embodiment, the diamond sheet 201 has a thickness of 0.03 millimeters (mm), a length within a range of 24 mm-26 mm, and a width within a range of 24 mm-26 mm, with a preferable length and width value of 25.4 mm. In other properties, diamond will have a density value within a range of 3400 Kilogram/cubic meter ($kg/m^3$)-3530 $kg/m^3$, a thermal conductivity value K within a range of 9000 Watt per meter kelvin (W/mk)-1500 W/mk, and a specific heat capacity, $C_p$, within a range of 620 Joule per kilogram kelvin (J/kgk)-650 J/kgk.

The high temperature sealing 205 is used to prevent leakages and attach the diamond sheet 201 to the pipeline 405. The high temperature sealing 205 can be, but is not limited to, a metal seal. Metal Seals are primarily used in static applications for temperatures as high as 1000° C./1832 Fahrenheit (° F.) and pressures as high as 6825 bar/99000 pounds per square inch (psi) for select applications. At low cryogenic temperatures and low pressures, such as vacuum seal applications, metal seals are far better than polymers since they do not become brittle and lose elasticity. Metal seals also have a low leakage rate down to $1\times10^{-12}$ cubic centimeters/sec per mm circumference, which in comparison to high load O-rings is almost 100× better. Unlike elastomer seals, metal seals are very highly resilient to corrosive chemicals and intense levels of radiation. Such resilience coupled with the right material selection/coating for an application, a metal seal can be a very durable seal performing dependably for an extended time.

In one embodiment, Polytetrafluoroethylene (PTFE) may be used in the high temperature sealing 205. PTFE can resist strong industrial chemicals, and maintain integrity at temperatures above 500-Fahrenheit (° F.). In a different embodiment, Polyether ether ketone (PEEK) may also be used in the high temperature sealing 205. PEEK can resist chemicals, wear, and abrasions. In a different embodiment, Fluorosilicone may be used in the high temperature sealing 205. Fluorosilicone combines high liquid resistance of fluorocarbon, and extreme temperature stability of silicone. With a temperature above 400° F., Fluorosilicone O-rings can be exposed to sunlight, and will not degrade due to air, ozone, aromatic, or chlorinated hydrocarbons. In a different embodiment, Silicone may be used as the high temperature sealing 205. Silicone, which is a rubber like polymer, has a high temperature resistance up to approximately 482° F. Furthermore, Silicone is resistant to UV rays, ozone, and oxygen and has great electrical insulation properties, and high gas permeability. Silicone is mainly used to manufacture aerospace seals, and automobile gaskets.

When considering the operating temperatures, Silicon, Fluorosilicone, and Fluorocarbon have an operating temperature within a range of 375° F.-500° F., with a preferable range of 400° F.-500° F. Ethylene Propylene Diene Monomer (EPDM) has an operating temperature within a range of 450° F.-500° F. with a preferable value greater than 400° F. Silicon sponge and conductive silicon have an operating temperature within a range of −100° F.-+500° F. Silicone Coated Fiberglass has an operating temperature of approximately 500° F./260° C. The clamping rim 203 used in the system of the present disclosure preferably fulfills the ISO-KF standards for clamp connections, DIN28404 and ISO 1609, which are the standards for vacuum pipes starting from the diameter nominal (DN), DN63, and larger diameters used in fine and high vacuum systems.

Preferably, the clamping rim 203 and the pipeline 405 are manufactured from the same material. For example, if the pipeline 405 is manufactured using Kanthal, the clamping 203 rim may also be manufactured from Kanthal. Using the same material for the clamping rim 203 and the pipeline 405 ensures that the clamping rim 203 can be conveniently attached to the pipeline 405 via adhesive or welding. An advantage of having the clamping rim 203 and the pipeline 405 made of the same material is that both the clamping rim 203 and the pipeline 405 will have the same rate of expansion when heated since both components share the same coefficient of thermal expansion. Therefore, significant development of stresses/strains that occur due to thermal expansion mismatch can be prevented by using the same material for the clamping rim 203 and the pipeline 405. However, if a secure connection can be established between the clamping rim 203 and the pipeline 405, the clamping rim 203 and the pipeline 405 may be manufactured from different material.

Figure 11:
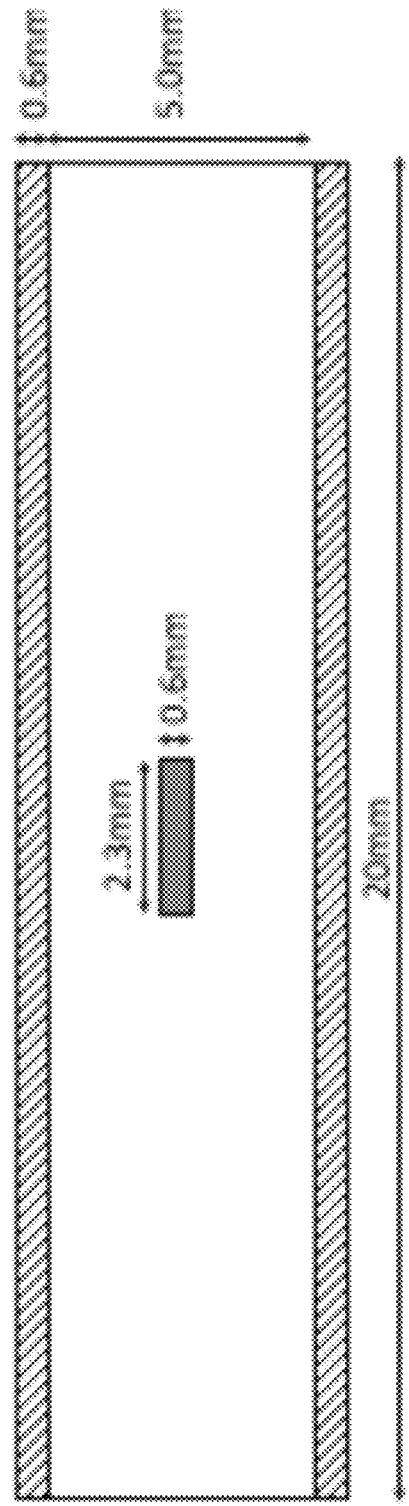
FIG. 11 is an illustration showing the dimensions used to model the thin diamond window assembly in computational fluid dynamics (CFD) analysis.

Computational fluid dynamic (CFD) simulation can be performed on the thin diamond window assembly 200 to verify the applicability of the system. As seen in FIG. 11, the dimensions of the diamond sheet 201, 0.6 mm×2.3 mm, are selected to simulate the use of the system of the present disclosure in medical computed tomography (CT) systems. In this instance, the power value of 10 kiloWatt (kW) is relatively high for a CT system corresponding to a 100 kiloVolt (kV) and 100 milliampere (mA) setting. The CFD simulation also gives information that the diamond sheet 201 will be sustained at a level well below the melting point.

Figure 12:
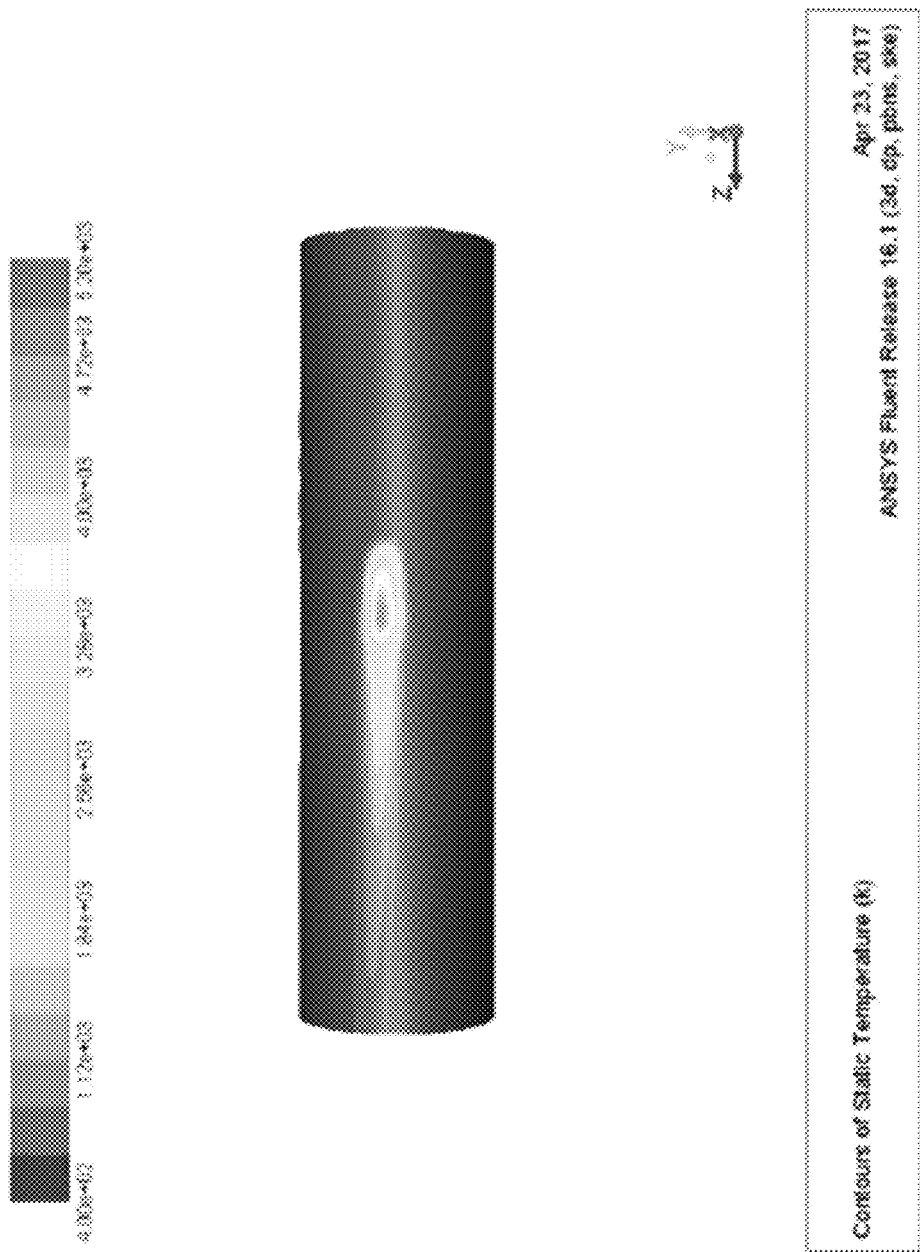
FIG. 12 is an illustration of the temperature distribution on liquid lead-bismuth eutectic with a fluid velocity 10 meters/sec (m/s).
Figure 13:
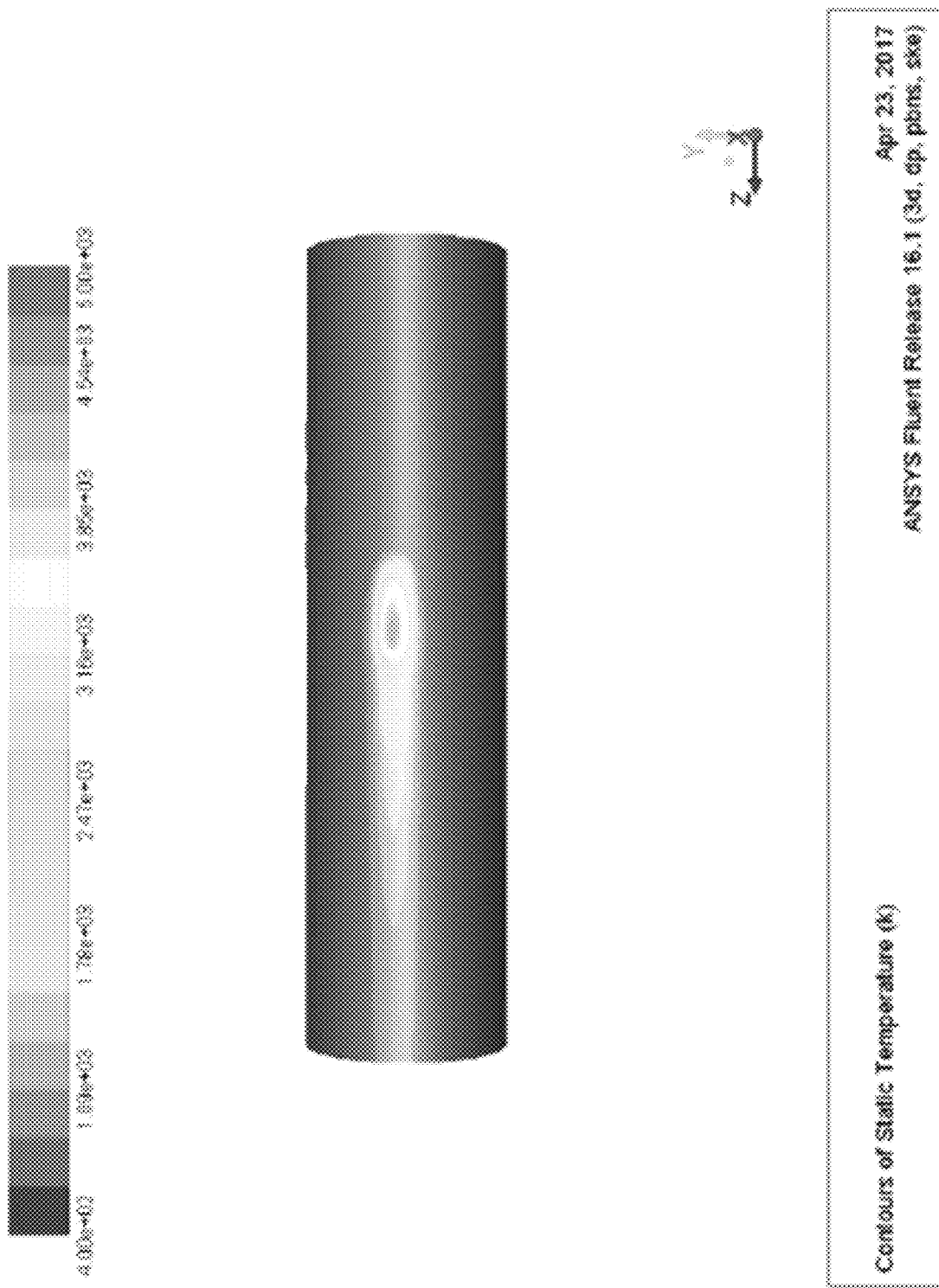
FIG. 13 an illustration of the temperature distribution on liquid lead-bismuth eutectic with a fluid velocity 50 m/s.

Furthermore, an inlet temperature of 400 K and an inlet velocity of 10 m/s and 50 m/s was considered during the simulation. The temperature distribution on the dynamic target material 411 at 10 m/s is shown in FIG. 12. The temperature distribution on the dynamic target material 411 at 50 m/s is shown in FIG. 13. The focal point where the electron beam collides with the dynamic target material 411 has a temperature of about 9000K, which may cause the liquid bismuth eutectic to locally evaporate. However, the flow of the dynamic target material 411 within the pipeline 405 allows the liquid bismuth eutectic to condense.

Figure 14:
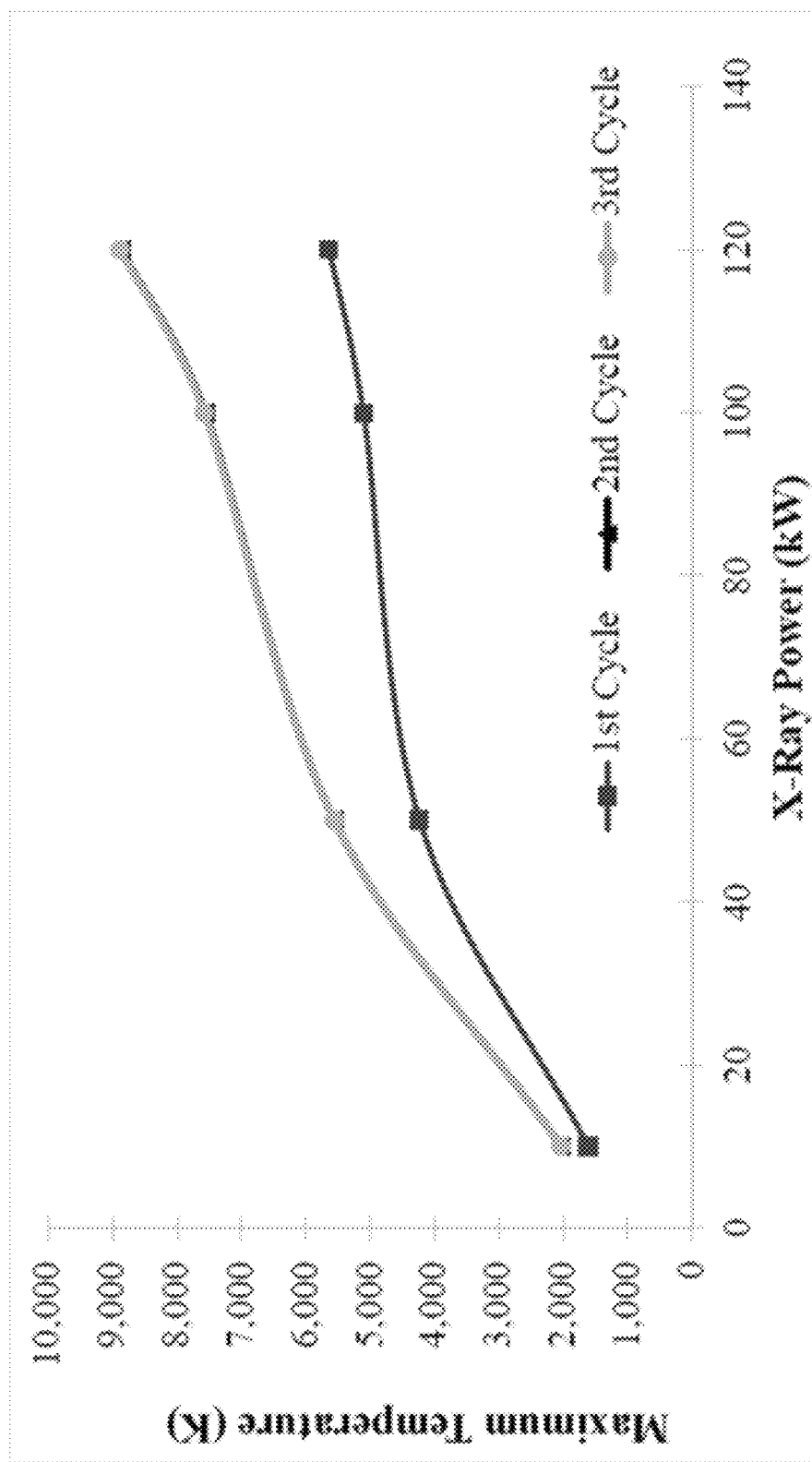
FIG. 14 is a graph illustrating the maximum temperature of the heating spot at different X-ray powers.
Figure 15:
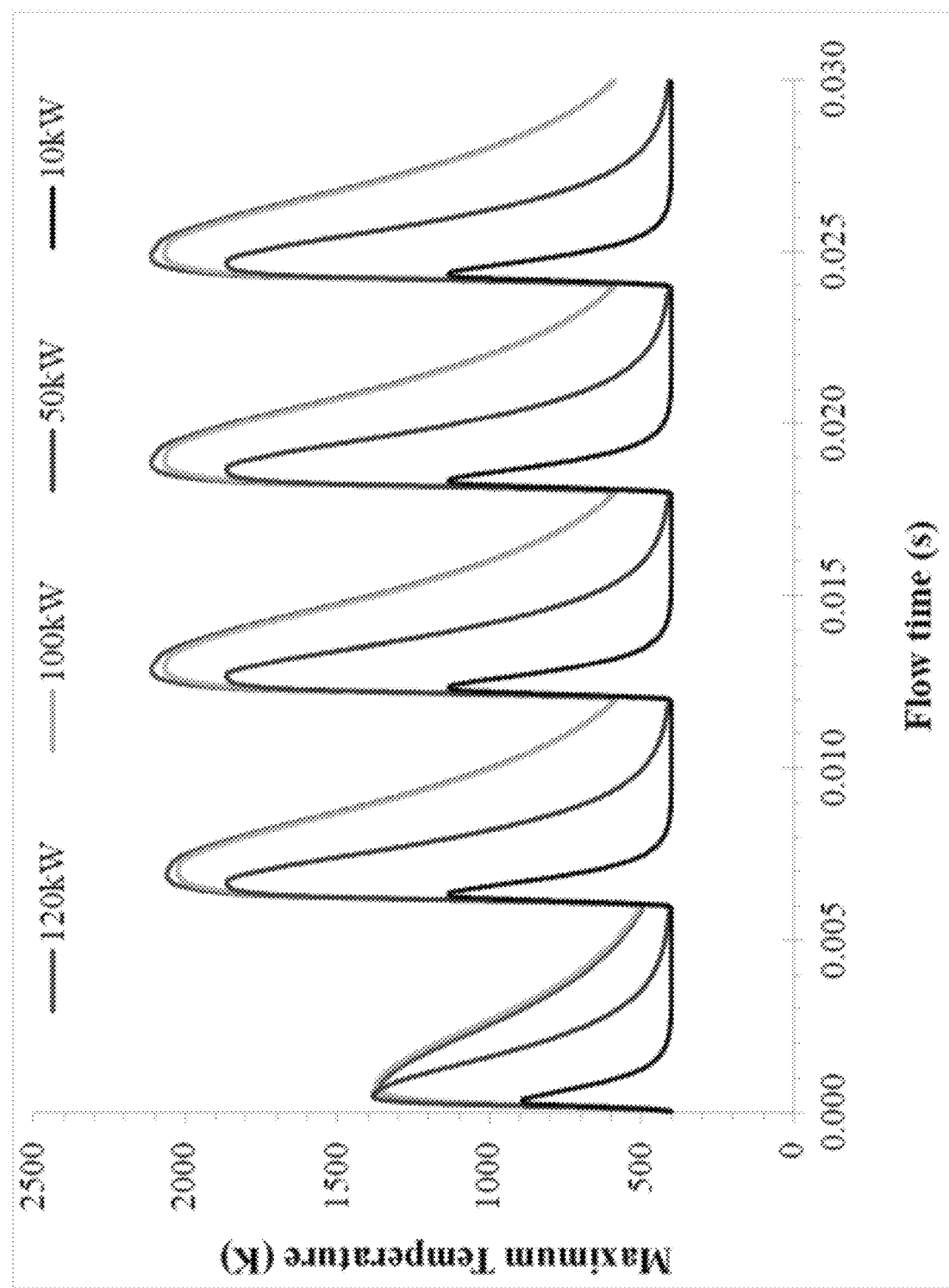
FIG. 15 is a graph illustrating the unsteady maximum temperature distribution of the thin diamond window assembly at different X-ray powers.
Figure 16:
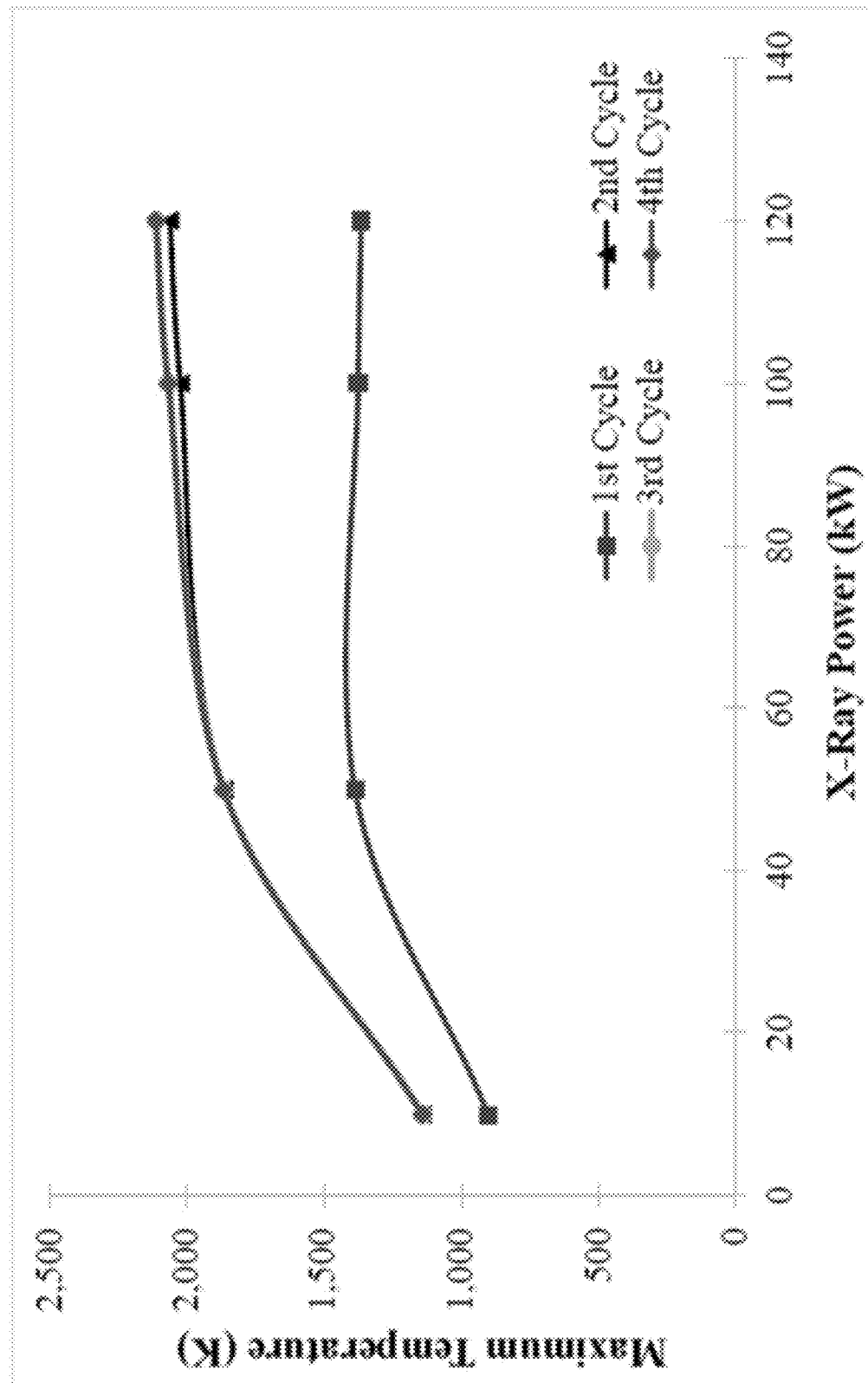
FIG. 16 is a graph illustrating the maximum temperature of the thin diamond window assembly at different X-ray powers.

In external boundary conditions, a majority of the target material flow system 400 was exposed atmospheric air and the dynamic target material 411 had a free stream temperature of 300 Centigrade (° C.). The dynamic target material 411 also had a heat transfer coefficient of 20 Watts per meter$^2$ kelvin (W/m$^2$-k). The heat inputs from the temperature control unit 409 can be, but is not limited to, 10 kW, 50 kW, 100 kW, and 120 kW wherein the heat transfer from the temperature control unit 409 to the dynamic target material 411 can be, but is not limited to, conduction, convection, and radiation. The maximum temperature of a focal spot on the diamond sheet 201 at different heat input values is shown in FIG. 14. From the calculations related to the CFD simulation, an increase in X-ray beam generation of approximately 12% is calculated. The maximum unsteady and steady temperatures of the diamond sheet 201 with time is shown in FIG. 15 and FIG. 16, and as seen in the figures the maximum unsteady and steady temperatures for the diamond sheet 201 is approximately 1100K for 10 kW is below the melting point for diamond which is 3000K. However, the temperature of the diamond sheet 201 at 120 kW is 2000K which is still below the melting temperature.

The X-ray generation enhancement obtained when the system of the present disclosure is used can be calculated as follows:
Atomic number of lead bismuth eutectic=(82*0.445+83*0.555)=82.555, wherein 82 is the atomic number of lead and 83 is the atomic number of bismuth. Furthermore, 44.5% is the percentage of lead in lead bismuth eutectic and 55.5% is the percentage of bismuth in lead bismuth eutectic. Next, the X-ray generation enhancement is calculated by comparing the atomic number of lead bismuth eutectic with the atomic number of tungsten, which is 74, as follows: 82.555/74=1.116=1.12. The value is approximately 12% higher in Z number, wherein the X-ray generation from electrons interacting with the dynamic target material 411 is linear with the atomic number of the dynamic target material 411.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

Obviously, numerous modifications and variations of the present invention are possible in light of the above teachings. It is therefore to be understood that within the scope of the appended claims, the invention may be practiced otherwise than as specifically described herein.

The invention claimed is:

1. A system for generating X-ray beams from a liquid target, comprising:
a vacuum chamber connected to a vacuum pump configured to reduce a pressure inside the vacuum chamber, wherein the vacuum chamber comprises an X-ray exit window;
a thin diamond window assembly, wherein the thin diamond window assembly is positioned within the vacuum chamber;
an electron source, wherein the electron source emits an electron beam towards the thin diamond window assembly, wherein the electron source is positioned within the vacuum chamber and the electron beam is aligned with the thin diamond window assembly;
a target material flow system, wherein a molten alloy which is in thermal communication with a temperature control unit of the target material flow system passes into and out of the vacuum chamber along a pipeline of the target material flow system, wherein the molten alloy is a dynamic target material of the target material flow system;
wherein the thin diamond window assembly is integrated into the target material flow system, wherein the beam of electrons contacts the dynamic target material through a diamond sheet of the thin diamond window assembly;
the thin diamond window assembly being angularly positioned to the electron beam, wherein the thin diamond window assembly allows the electron beam to pass through and collide with the dynamic target material to generate an X-ray beam, wherein the angular positioning of the thin diamond window assembly allows the generated X-rays to be emitted towards the X-ray exit window;
an X-ray detector/imager, wherein the X-ray detector/imager is positioned externally and adjacent the vacuum chamber; wherein the X-ray detector/imager is positioned perpendicular to a projection path of the electron beam from the electron source; and
the X-ray detector/imager being aligned with the X-ray exit window, wherein the electron source, the diamond window, the target material flow system and the X-ray exit window are positioned with respect to each other so that an X-ray beam generated at the thin diamond window assembly passes through the X-ray exit window toward the X-ray detector/imager passing through an imaging subject.

2. The system for generating X-ray beams from a liquid target of claim 1, wherein the target material flow system comprises a circulation pump, a reservoir, the pipeline, the temperature control unit, and the dynamic target material,
wherein the temperature control unit maintains a temperature of the dynamic target material to be above a melting point temperature;
the dynamic target material being in fluid motion within the pipeline;
the dynamic target material being in thermal communication with the temperature control unit;
the reservoir and the circulation pump being in fluid communication through the pipeline; and
the reservoir, the circulation pump, and the pipeline being in direct contact with the temperature control unit.

3. The system for generating X-ray beams from a liquid target of claim 2, wherein the temperature control unit comprises a heating coil, wherein the heating coil is wrapped around the reservoir, the circulation pump, and the pipeline.

4. The system for generating X-ray beams from a liquid target of claim 1, wherein the dynamic target material is a lead bismuth eutectic.

* * * * *